(12) United States Patent
Hamuro et al.

(10) Patent No.: US 7,378,387 B2
(45) Date of Patent: *May 27, 2008

(54) METHOD OF SUPPRESSING IMMUNE RESPONSE BY REDUCING INTRACELLULAR CONTENT OF GLUTATHIONE IN MACROPHAGES AND MONOCYTES

(75) Inventors: Junji Hamuro, Kanagawa-ken (JP); Yukie Murata, Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/097,146

(22) Filed: Apr. 4, 2005

(65) Prior Publication Data

US 2005/0239886 A1 Oct. 27, 2005

Related U.S. Application Data

(63) Continuation of application No. 09/731,830, filed on Dec. 8, 2000, now abandoned, which is a continuation of application No. 09/334,647, filed on Jun. 17, 1999, now Pat. No. 6,197,749, which is a continuation-in-part of application No. 09/191,881, filed on Nov. 12, 1998, now abandoned.

(30) Foreign Application Priority Data

Oct. 29, 1997 (JP) ............................... 09-312727
Oct. 29, 1998 (JP) ............................... 10-308300

(51) Int. Cl.
*A61K 38/00* (2006.01)

(52) U.S. Cl. ........................... 514/2; 514/18; 514/562; 530/351; 424/9.1; 424/85.1; 424/85.2; 424/85.4

(58) Field of Classification Search ................ 514/18, 514/562, 2; 530/351; 424/9.1, 85.1, 85.2, 424/85.4

See application file for complete search history.

(56) References Cited

U.S. PATENT DOCUMENTS

| | | | |
|---|---|---|---|
| 4,871,528 A | 10/1989 | Tognella et al. | |
| 5,087,453 A | 2/1992 | Strassmann | |
| 5,214,062 A | 5/1993 | Mark et al. | |
| H1427 H | 4/1995 | Briet et al. | |
| 5,441,976 A | 8/1995 | Andersson et al. | |
| 5,476,966 A | 12/1995 | Andersson et al. | |
| 5,488,040 A | 1/1996 | Jamas et al. | |
| 5,541,162 A | 7/1996 | Ohmori et al. | |
| 5,580,577 A | 12/1996 | Herzenberg et al. | |
| 5,627,152 A | 5/1997 | Kenyhercz et al. | |
| 5,747,459 A | 5/1998 | Rowe et al. | |
| 5,762,922 A | 6/1998 | Noble et al. | |
| 5,766,873 A | 6/1998 | Noble et al. | |
| 5,804,582 A | 9/1998 | Andersson et al. | |
| 6,077,828 A | 6/2000 | Abbruzzese et al. | |
| 6,197,749 B1 | 3/2001 | Hamuro et al. | |
| 2005/0239886 A1* | 10/2005 | Hamuro et al. | 514/550 |

FOREIGN PATENT DOCUMENTS

| | | |
|---|---|---|
| EP | 0 501 641 | 9/1992 |
| EP | 0 638 588 | 2/1995 |
| EP | 0 715 853 | 6/1996 |
| WO | WO 91/18594 | 12/1991 |
| WO | WO 95/06465 | 3/1995 |

OTHER PUBLICATIONS

M. Roederer, et al., "CD4 and CD8 T Cells with High Intracellular Glutathione Levels are Selectively Lost as the HIV Infection Progresses", International Immunology, vol. 3, No. 9, pp. 933-937, 1991.

E. Sherwood, et al., "Enhancement of Interleukin 1 and Interleukin 2 Production by Soluble Glucan", Int. J. Immunopharmacol., vol. 9, No. 3, pp. 261-268, Abstract.

S. Tsuyyuki, et al., XP-002223987, "Possible availability of N-acetylcysteine as an adjunct to cytokine therapy for hepatocellular carcinoma", Clinical Immunology and Immunopathology, vol. 88, No. 2, Aug. 1998, pp. 192-198.

J. Peterson, et al., XP-002223988, "Glutathione Levels in Antigen-Presenting Cells Modulate Th1 Versus Th2 Response Patterns", Proceedings of the National Academy of the Sciences of the United States, vol. 95, No. 6, Mar. 17, 1998, pp. 3071-3076.

M. Sato, et al., XP-002067027, "Antioxidants Inhibit Tumor Necrosis Factor-α Mediated Stimulation of Interleukin-8, Monocyte Chemoattractant Protein-1, and Collagenase Expression in Cultured Human Synovial Cells", The Journal of Rheumatology, 1996, vol. 23, No. 3, pp. 432-438.

R. Ruffmann, et al., XP-001051483, "GSH Rescue by N-Acetylcystein", Klin Wochenschr, 1991, vol. 69, pp. 857-862.

J. Hamuro, XP-001120690, "Lentinan Regulates the Local Inflammatory Cellular Reaction at Tumor Tissues-Its Relation with Antitumor Effects", Biotherapy, vol. 10, No. 4, Apr. 1996, pp. 581-588.

M. Anderson, XP-002223989, "Glutathione: An Overview of Biosynthesis and Modulation", Chemico-Biological Interactions, 111-112, 1998, pp. 1-14.

P. Parodi, XP-000750365, "A Role for Milk Proteins in Cancer Prevention", The Australian Journal of airy Technology, vol. 53, Apr. 1998, pp. 37-47.

J. Hamuro, et al., XP-009002330, "The Triggering and Healing of Tumor Stromal Inflammatory Reactions By Oxidative and Reductive Macrophages", Gann Monograph on Cancer Research, vol. 48, 1999, pp. 153-164.

(Continued)

Primary Examiner—Chih-Min Kam
(74) Attorney, Agent, or Firm—Oblon, Spivak, McClelland, Maier & Neustadt, P.C.

(57) ABSTRACT

A method of suppressing immune responses, comprising administering to a patient in need thereof an effective amount of a composition comprising a substance capable of reducing the content of reductive glutathione in macrophages.

22 Claims, 4 Drawing Sheets

OTHER PUBLICATIONS

C. Yim, et al., "Use of N-Acetyl Cysteine to Increases Intracellular Glutathione During the Induction of Antitumor Responses by IL-2[1]", Journal of Immunology, vol. 152, No. 12, 1994, pp. 5796-5805.

K. Dobashi, et al., "Regulation of LPS Induced IL-12 Production by IFN-γ and IL-4 through Intracellular Glutathione Status in Human Alveolar Macrophages", Clin. Exp. Immunol., 2001, vol. 124, pp. 290-296.

H. Minhas, et al., "Comparison of th Delivery of Reduced Glutathione into P388D, Cells by Reduced Glutathione and Its Mono- and Diethyl Ester Derivatives", Biochemical Pharmacology, vol. 49, No. 10, 1995, pp. 1475-1782, XP002234498.

E. Sherwood, et al., "Enhancement of Interleukin 1 and Interleukin 2 Production by Soluble Glucan", Int. J. Immunopharmacol., vol. 9, No. 3, pp. 261-268, Abstract, 1987.

* cited by examiner

Th1/Th2 balance and reductive/oxidative macrophages (MΦ)

METHOD OF SUPPRESSING IMMUNE RESPONSE BY REDUCING INTRACELLULAR CONTENT OF GLUTATHIONE IN MACROPHAGES AND MONOCYTES

CONTINUING APPLICATION DATA

The present application is a Continuation of U.S. application Ser. No. 09/731,830, filed Dec. 8, 2000, now abandoned, which is a Continuation of U.S. application Ser. No. 09/334,647, filed Jun. 17, 1999, now U.S. Pat. No. 6,197,749, issued Mar. 6, 2001, which is a Continuation-in-Part of U.S. application Ser. No. 09/191,881, filed Nov. 12, 1998, now abandoned.

BACKGROUND OF THE INVENTION

1. Field of the Invention

The present invention relates to a novel immunomodulator. More specifically, the present invention relates to an immunomodulator (e.g., immunoenhancer and immunosuppressant) capable of oral intake which has a novel suppressive function on macrophages (hereinafter sometimes abbreviated as "MΦ") or monocytes and which may be used, for example, for the treatment, improvement and prevention of human immunological diseases such as hepatic cirrhosis, hepatitis, diabetes, gastrointestinal inflammatory diseases such as inflammatory bowel diseases (ulcerative colitis, Crohn disease, etc.), auto-immune diseases and allergic diseases such as hypersensitive interstitial pneumonia, pulmonary fibrosis, chronic rheumatoid arthritis, asthma and cutaneous atopy, and cancers, and to a drug, a food (including a food for medical care, a health food or a special sanitary food), a nutrient and an infusion containing the same.

2. Description of the Related Art

As used herein, the term immune system refers to a system in an organism for defending itself from exogenous infection with virus, bacteria or the like, or from invasion of a human body with transformed cells (tumor cells and the like) formed by transformation of autologous cells. However, the immune system occasionally behaves abnormally, i.e., it functions excessively and acts to reject autologous components, or, on the other hand it sometimes functions deficiently, resulting in an immunocompromised state. Diseases resulting from these abnormal responses are generally called immunological diseases. Examples thereof include diverse diseases, for example, acute or chronic inflammatory diseases such as atopic cutaneous inflammatory diseases, pollinosis, asthma and sarcoidosis; autoimmune diseases such as allergic diseases, chronic rheumatoid arthritis, diabetes (IDDM), SLE and chronic fatigue syndrome; hepatitis, hepatic cirrhosis, inflammatory bowel diseases (IBD) such as ulcerative colitis and Crohn disease; and cancer cachexia. These immunological diseases originate from complex pathological causes. Systemic immunodeficiency and functional deficiency originate from pathological inflammation accompanied by cell proliferation, differentiation or cell necrosis through local production of cytokines or inflammatory mediators.

As cells that participate in immunity, T lymphocytes and B lymphocytes are well known. These cells exhibit a wide variety of functions as cells playing roles in cellular immunity and humoral immunity respectively. Meanwhile, macrophages and monocytes are cells that are intimately involved in both cellular immunity and humoral immunity, and they participate significantly in rejection of non-self foreign bodies, for example, in immunological diseases such as allergy and rheumatism, cancers and bacterial infection.

The functions of macrophages and monocytes are classified into four different types, a secretary function, an immunoregulatory function (mainly antigen presentation), treatment of foreign bodies and waste matters, a phagocytic function and a cytotoxic/cytostatic activity against target cells. It is widely accepted that these cells produce diverse inflammatory mediators; for example cytokines such as TNF, IL-12, IL-1, IL-6, TGFβ and IL-8 and so on; hormonal molecules such as neopterine (NPT) and dihydroxyepiandrosterone (DHEA); arachidonic acid metabolites such as PGE2 and LTB4; complement and related molecules such as C5a and C3; such as reactive oxygen and reactive nitrogen intermediates. It has not been clarified whether these diverse functions are exhibited by one kind of macrophage or monocyte or by distinctive groups of macrophages or monocytes having different functions. While lymphocytes are classified into distinctive subsets according to their cell surface markers and the distinctive functional markers uniquely correspond to each subset of lymphocyte, the correspondence between the wide variety of functions of macrophages is less clear. Monocytes have not been classified into cellular subsets. For this reason, although macrophages and monocytes play quite important roles in the triggering and the pathological progression of the above mentioned inflammatory, allergic and immunological diseases, the functional classification of macrophages and monocytes subsets has not yet been applied at all to therapeutic, prophylactic and preventive treatment of human diseases, with the assumption of the presence of macrophage and monocyte subsets, and even the hypothesis thereof has not yet been given.

In recent years, in the patients suffering from allergic diseases, autoimmune-diseases such as chronic rheumatoid arthritis and cancer, the inclination of helper T cell subsets in the peripheral blood has been pointed out and has been linked to the pathology of these diseases. Helper T lymphocytes which are a subset of T lymphocytes have been further classified into two subsets, namely Th1 and Th2, and it is currently proving that the ratio of these two types is an relevant index of immunological functions of patients. Attempts are being made to establish a more appropriate therapeutic treatment by diagnosis of the ratio or by improvement of the ratio based on this index. That is, it is known that when the amount of Th2 inducing IgE production from B cells is higher than that of Th1 (Th1<Th2), allergic diseases are worsened. Attempts are being made to suppress allergy upon measuring a Th1/Th2 ratio to examine an immunological response of patients or to provide Th1 response superior to Th2 responses. On the contrary, the presence of diseases caused by a predominance of Th1 has been successively indicated also in chronic rheumatoid arthritis or an asthmatic inflammatory disease at the chronic stage.

Even when the Th1/Th2 balance is measured using biological materials and the functions of the two subsets are modulated, this modulation has not successfully been utilized currently in the examination or the diagnosis of local chronic inflammatory diseases or allergic diseases. The terms such as Th1 diseases and Th2 diseases have been used lately. However, these terms cannot necessarily be distinguished clearly.

The Th1/Th2 presence ratio is only an index of lymphocyte subsets. Since the in vivo dynamism of the lymphocyte subsets is actually regulated by the cell group called accessory cells including macrophages in the present invention, it is difficult to appropriately diagnose the progression of diseases with only the Th1/Th2 presence ratio and to treat the same on the basis of this index. As will be described below, the Th1/Th2 balance is controlled by the distinct macrophage/monocytes functions. Even if a skewing to Th1>Th2 is intended, this is hardly effective for therapy of immunological diseases, due to the presence of a complex cytokine network, and a new index for diagnosis and therapy has been in demand.

It has been clarified that in macrophages participating in the inflammatory reactions, the functions of the cells are variable depending on environmental factors such as oxidative stress, cytokine stimulation, infection with virus or bacteria and the like. However, the correspondence between the functions and the classification of cell subsets of macrophages is highly uncertain. New findings are required in the above-mentioned classification of functions and subsets, and these findings will lead to the development of quite useful new therapeutic methods. Under such circumstances, the development of excellent agents for modulating immunity, namely, immunomodulators, has been in demand.

SUMMARY OF THE INVENTION

It is an object of the present invention to provide a method of suppressing immune responses.

It is another object of the present invention to provide compositions, especially food compositions, which may be used to suppress immune responses.

The present inventors have conducted investigations to solve the above-mentioned problems, and have consequently found the following findings. That is, they have attempted to distinguish macrophages (including monocytes) which share with an immunosuppressive activity, a cachexia inducing activity, an activity of inducing malignant progression and an activity of prolonging inflammation from immunoregulatory macrophages in view of a difference in a redox state (potential) of macrophages, and have then succeeded in this attempt. The reductive glutathione (GSH) content in macrophages is employed as an index thereof.

Accordingly, the objects of the present invention, and others, may be accomplished with method of suppressing immune responses by administering to a patient in need thereof an effective amount of a composition comprising a substance capable of reducing the content of reductive glutathione in macrophages.

BRIEF DESCRIPTION OF THE DRAWINGS

A more complete appreciation of the invention and many of the attendant advantages thereof will be readily obtained as the same becomes better understood by to the following detailed description when considered on combination with the accompanying drawings, wherein.

DETAILED DESCRIPTION OF THE PREFERRED EMBODIMENTS

Glutathione is present in all mammalian cells, and well known as an intrinsic antioxidant. It is a tripeptide having a wide variety of functions in cells, such as removal of radicals or peroxides, metabolism of eicosanoids such as prostaglandin, detoxication of biologically foreign materials, amino acid transport and the like. Glutathione includes reductive glutathione (GSH) and oxidative glutathione (GSSG), and these form a coupled cycle. In normal cells, the content of reductive glutathione (GSH) is higher, and it acts defensively on oxidative stress, especially on $H_2O_2$.

Ruede et al. have already reported that with respect to macrophages differentiated in the presence of GM-CSF and macrophages differentiated in the presence of M-CSF from monocytes, the cellular GSH content of the former is higher than that of the latter, so that the difference in the GSH content in cells seems likely to participate in the function of macrophages (Germann, T., Mattner, F., Partenheimer, A. et al.: Different accessory function for Th1 cells of bone marrow derived macrophages cultured in granulocyte-macrophage colony-stimulating factor or macrophage colony-stimulating factor. Int. Immunol., 4:755, 1992: Frosch, S., Bonifas, U., Eck, H. P. et al.: The efficient bovine insulin presentation capacity of bone marrow-derived macrophages activated by granulocyte-macrophage colony-stimulating factor correlates with a high level of intracellular reducing thiols. Eur. J. Immunol., 23; 430, 1993). The present inventors have measured the reductive GSH content in macrophages, and have found that there is a great difference in an immunological function between macrophages having different GSH contents (refer to FIG. 1); they have tested the immune responses with regards to the cellular GSH content, and have found that the redox states can artificially be modulated with an orally administerable low-molecular weight substance, and that these substances capable to modulate intracellular GSH content can widely be applied to treatment of wide variety of diseases and the substance can be also used as a food (refer to FIG. 1). These findings have led to the completion of the present invention.

Figure 1:
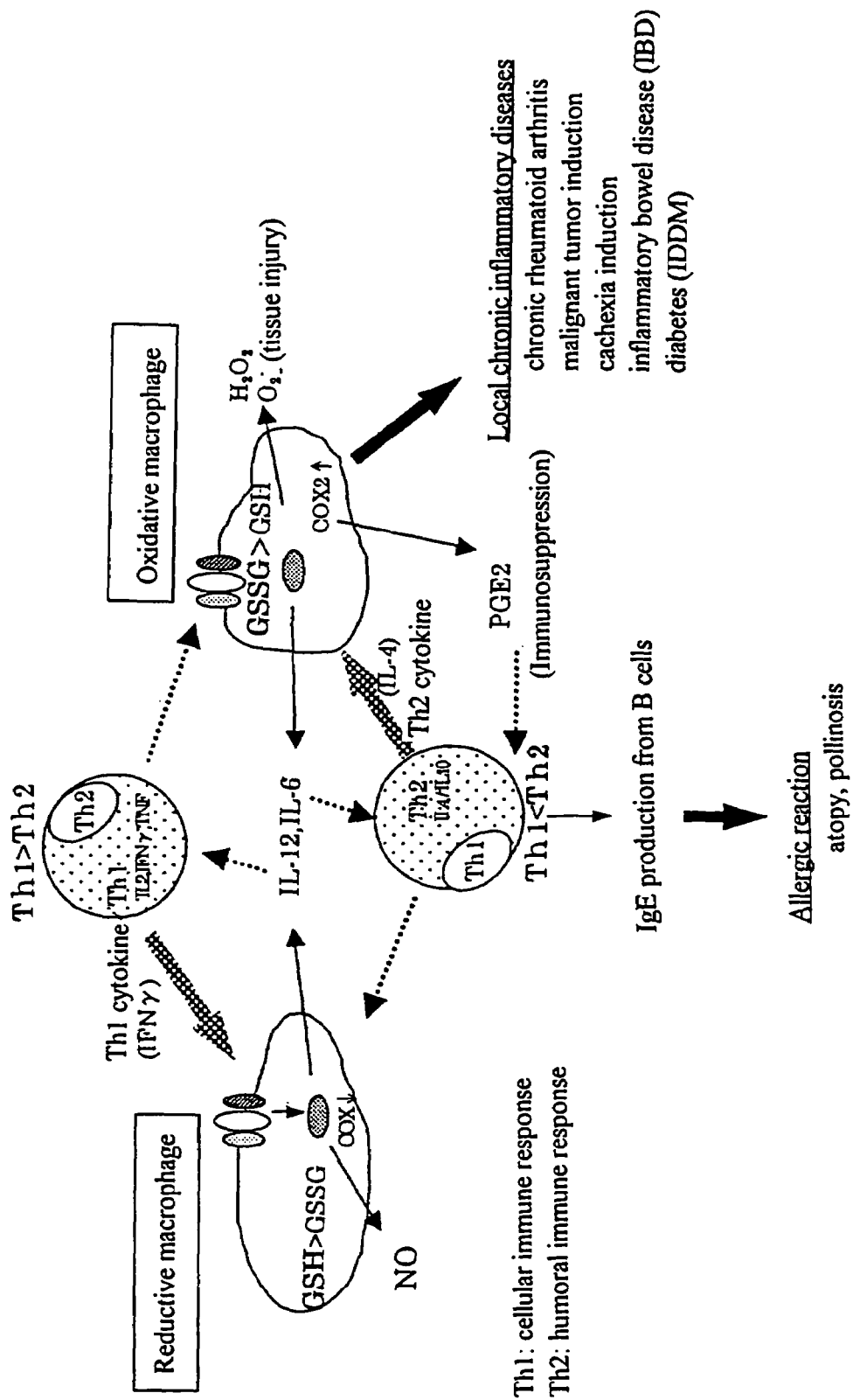
FIG. 1 is a diagrammatic view showing a relationship of a difference in a function of macrophages, with respect to the Th1 and Th2 balance, immunosuppression, malignant progression, cancer cachexia, and local inflammatory responses.

FIG. 1 is a diagrammatic view showing a linkage between a difference in a function of macrophages or monocytes (both are referred to as "macrophages" in the present invention), and an effect on a Th1/Th2 balance, a mechanism of immunosuppression, cachexia induction and induction of malignant tumor progression caused by a functional difference of macrophages and local inflammatory diseases. For example, according to the tumor progression, the local Th1/Th2 balance is skewed, an inclination to humoral immunity appears, the structure and the function of the cytokine receptor complex are changed, oxidative macrophages with a low intracellular GSH content are increased, the production of active oxygen or inflammatory mediators such as PGE2, IL-6, IL-10 and IL-8 are increased to cause systemic immunosuppression or induction of cachexia and to prolong chronic inflammation accompanied by allergic reactions or tissue injury.

The present inventors have conducted further investigations on the basis of the above-mentioned findings, and have consequently found that heterogeneous macrophages, which play important roles in the inflammation reactions can be classified into two groups, namely, oxidative macrophages and reductive macrophages by determining the intracellular content of oxidative glutathione and the intracellular content of reductive glutathione in macrophages. The oxidative macrophages induce local chronic inflammatory diseases or an allergic reaction in immunological diseases and the Th1/Th2 balance controlling the balance of humoral and cellular immunity is regulated with the redox state of macrophages, that the redox state of the macrophages plays an important role in immunological diseases, and this redox state is monitored and artificially controlled or modified which is useful in the diagnosis or the therapy of these immunological diseases, and that this control can easily be conducted using low-molecular weight substances capable of oral intake.

With respect to the definition of the oxidative macrophage and the reductive macrophage in the present invention, macrophages are reacted with monochlorobimane which is a chemical reagent specific to reductive glutathione (GSH) to determine the GSH content in cells. A macrophage having a GSH content which is higher in comparison with the resident macrophages is defined as a reductive macrophage, and a macrophage having a GSH content which is lower is defined as an oxidative macrophage. Further, a macrophage in which the GSH content becomes more than 2 nmoles/5×$10^5$ macrophages by bringing a low-molecular weight substance capable of oral intake into contact with the macrophage for from 2 to 24 hours is defined as the reductive macrophage (or monocyte), and a macrophage in which the GSH content becomes less than 0.1 nmoles/5×$10^5$ macrophages is defined as the oxidative macrophage. Alternatively, a macrophage of which the GSH content is two or more times than that of the resident macrophage is defined as a reductive macrophage, and a macrophage of which the GSH content is 1/5 or less that of the resident macrophage is defined as an oxidative macrophage.

At present, it is considered that the Th1/Th2 balance is regulated by the ratio of IL-6 or IL-4 and IL-12 produced in vivo. It is known that Th2 participating in humoral immunity is induced by the former two and Th1 by IL-12 respectively. It is clarified that IL-6 and IL-12 are produced from macrophages. However, assuming that the same macrophages produce both IL-6 and IL-12, one type of a macrophage participating in both the Th1 induction and the Th2 induction comes to be present. Thus, there is a great contradiction in considering the host immune responses.

Figure 2:
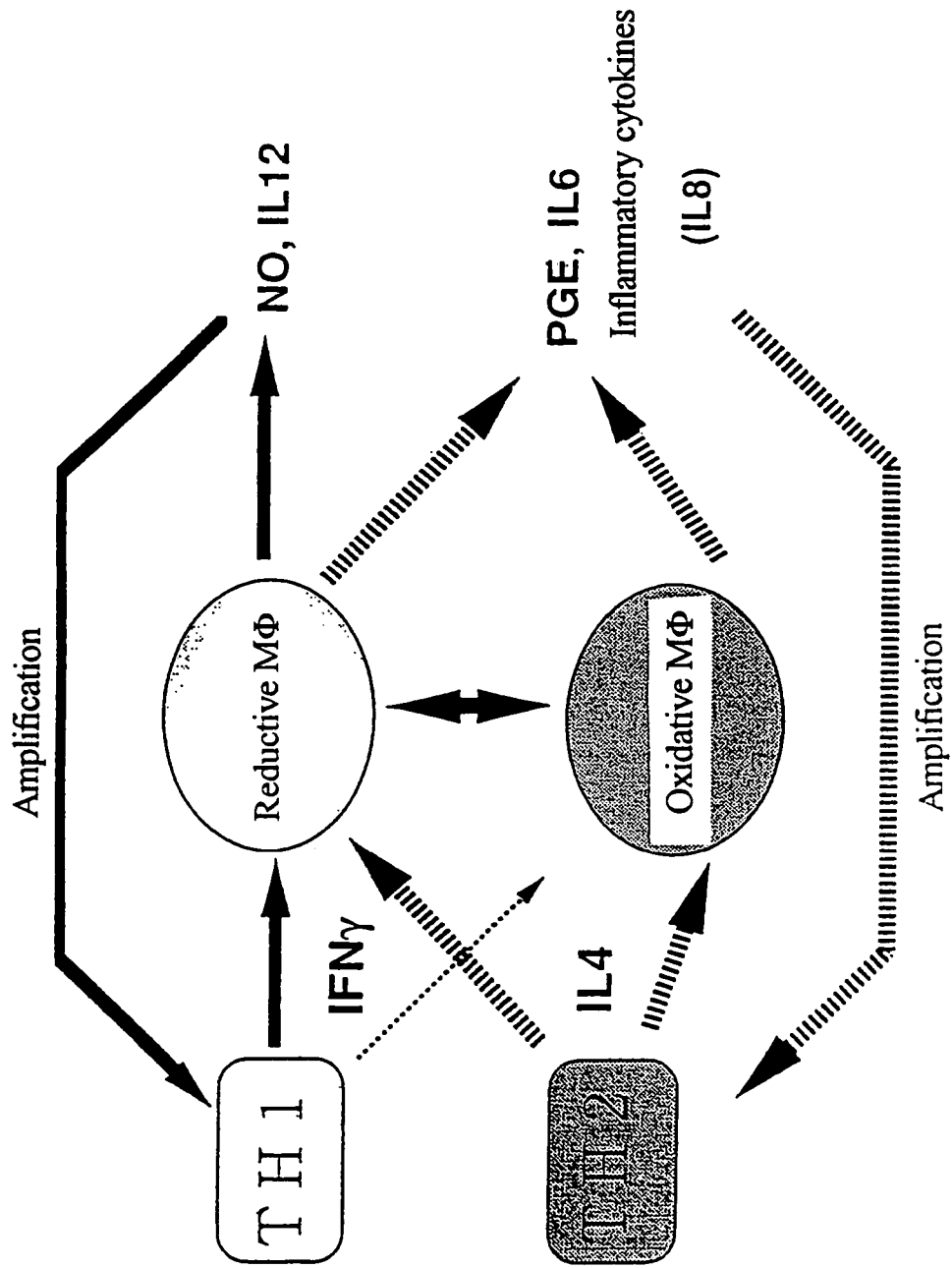
FIG. 2 illustrates that the presence ratio of oxidative and reductive macrophages controls the immunological functions through the skewed generation of Th1 and Th2 cytokines. This is based on the new findings of the present inventors, showing that the redox condition of macrophages plays an important role in amplifying the inclination of the in vivo responses between humoral and cellular immunity.

The present inventors have found that IL-12 is produced from only the reductive macrophage having the high intracellular GSH content to act on the Th1 induction and that the IL-6 production is increased in the oxidative macrophage to induce Th2. They have further found that when the macrophage is inclined to the oxidative type in spite of the production of IFNγ, a typical Th1 cytokine, IL-6 skewing the balance to Th2 is produced in a large amount by IFNγ stimulation. On the contrary, it has also been found that IFNγ, a typical Th1 cytokine, increases the phenotype of the reductive macrophage further by acting on the reductive macrophage. When IL-4, the typical Th2 cytokine, acts on the oxidative macrophage, the oxidative macrophage phenotypes are further increased. These knowledge indicate that the balance between humoral immunity and cellular immunity is unequivocally defined by the redox state of macrophages, and they are relevant new findings innovating the basic concept of immunology (refer to FIG. 2). On the basis of these findings, the quite useful, original invention overcoming the conventional confused immunological disease therapy was already completed with respect to the diagnosis and the therapy of the immunological diseases. Investigations have been assiduously conducted on the basis of the above-mentioned findings. Consequently, the present invention has been newly completed.

That is, the present invention is an immunomodulator containing substances having an activity of changing a content of glutathione in macrophages. In the present invention, the macrophage also includes monocytes. This substance is preferably one which provide MΦ with productivity of interleukin 12 by increasing the content of reductive glutathione in macrophages. More preferable examples thereof include low-molecular weight substances, for example, a GSH precursor metabolized into GSH within cells, such as N-acetylcysteine (NAC), γ-glutamylcysteine, γ-glutamylcysteine dimethyl ester, γ-glutamylcysteine diethyl ester and N-acetylcysteine nitroxybutyl ester; glutathione derivatives such as glutathione monoester, glutathione diester and glutathione nitroxybutyl ester; lipoic acid and derivatives thereof; gliotoxin and derivatives thereof having two SH groups or more in the molecule; and ortene. These can be administered orally or percutaneously. It is also possible to use antioxidants such as flavonoid and derivatives thereof which raise the GSH content, increase the production of IL-12 and decrease the production of IL-6 by contact with macrophages. Further, high-molecular weight substances which are used in combination therewith, such as β(1-3) glucan and cytokine, are preferably used in the intravenous administration and the administration using DDS (drug delivery system). Preferable examples of the cytokine include IL-4, IL-2, IL-12, TGFβ and IFNγ. When it is required to increase cellular immunity, IL-2 and/or IFNγ is especially preferable. When it is required to decrease cellular immunity, IL-4 and/or TGFβ is especially preferable. These substances can be contained either solely or in combination, and a higher effect is expected by a combination of a low-molecular weight orally administerable immunomodulator and a high-molecular weight immunomodulator suited for intravenous administration.

Further, the present invention also includes an immunomodulator containing a substance which can selectively remove either of two types of macrophages, reductive macrophages or oxidative macrophages which are different in the intracellular content of reductive glutathione. Examples of the substance include a substance in which a cytotoxic DNA alkylating agent is conjugated with glutathione, and a substance in which an oxidative or reductive macrophage-specific antibody is conjugated directly or through a linker with a low-molecular weight compound having a cytotoxicity to macrophages or with a material showing a cytotoxicity after being incorporated into a macrophage. Examples of the alkylating agent include cyclophosphamide, nimustine (ACNU), mitomycin C and melphalan. In an oxidative macrophage in which glutathione S-transferase is activated, an DNA alkylating agent, bound to glutathione directly or through a linker, is deconjugated by the action of this enzyme and can remove the reductive macrophage by specifically killing the same. Further, a substance which has no cell-killing property in vitro but comes to show the cell-killing property with the action of an enzyme increased either in oxidative or reductive macrophages can also be used as a prodrug.

The present inventors have conducted further investigations especially on gastrointestinal inflammatory diseases based on these findings, have looked for substances of reducing a content of reductive glutathione in macrophages, and have found substances which exhibit the effect at quite low doses. They have produced animal models having gastrointestinal inflammatory diseases similar to those of humans, and have promoted their investigations for development of an immunosuppressant as a drug, and a food such as a food for medical care, a health food or a special sanitary food, a nutrient and an infusion which have an immunosuppressive activity. They have focused on cystine derivatives, and have widely examined an effect of inhibiting an immunological activity in vitro and an immunosuppressive effect in the administration to animals using a compound represented by the following structural formula (1), as well as a pharmaceutical effect of candidate substances using gene knock out mice which are spontaneously accompanied with gastrointestinal inflammatory diseases. Consequently, they have found that cystine derivatives, especially those represented by the following structural formula (1) are effective as pharmaceutical substances having an activity of reducing the content of reductive glutathione in macrophages and monocytes.

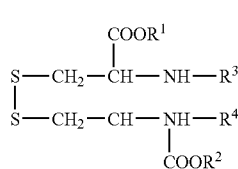
(I)

wherein $R^1$ and $R^2$, independently from each other, represent an alkyl group or a substituted alkyl group such as the nitroxybutyl group, and $R^3$ and $R^4$, independently from each other, represent an acyl group or a peptidyl group.

Especially, it is quite useful as an immunosuppressant against inflammatory bowel diseases such as ulcerative colitis and Crohn disease, and gastrointestinal inflammatory diseases such as hepatitis and hepatic cirrhosis.

Further, the present invention includes a food (including a food for medical care, a health food or a special sanitary food), a nutrient or an infusion containing the above-mentioned immunomodulator. The food includes ordinary foods and those which are put into the mouth, such as a toothpaste, a chewing gum and the like. It is especially preferable to incorporate the immunomodulator in health foods. Further, it may be used as an additive which is added to a food. As the nutrient, vitamin preparations and calcium preparations are available. As the infusion, a high calorie infusion, a physiological saline solution and blood preparations are available.

In addition, the immunomodulator, the food, the nutrient and the infusion of the present invention is preferably used for improvement of the cachectic condition of patients suffering from cancers and for diabetes, gastrointestinal inflammatory diseases, chronic rheumatoid arthritis, hepatitis, hepatic cirrhosis, above stated autoimmune inflammatory diseases and/or chemoprevention of cancers.

Especially, an immunomodulator having an activity of reducing a content of reductive glutathione in macrophages of humans can widely be used in not only drugs but also the foods as an immunosuppressant of the autoimmune inflammatory diseases in the form of a single compound or a mixture. Thus, it is useful as the food, the nutrient and the infusion having the immunosuppressive activity.

The present invention is described in even more detail below.

The present invention provides an immunomodulator useful for therapy of patients suffering from immunological diseases in which macrophages are classified into oxidative macrophages and reductive macrophages having different functions by determining the contents of oxidative glutathione and/or reductive glutathione in macrophages using a body fluid or a cell sample separated and collected from humans, and the ratio of these macrophages present is artificially controlled with a substance capable of oral intake or either oxidative macrophages or reductive macrophages are artificially removed, as well as to a food, a nutrient and an infusion which are useful for improvement of diseases. With respect to the body fluid/cell samples separated and collected from humans, there are, for example, cells separated from the peripheral blood, the peritoneal cavity, the thoracic cavity, the solid carcinoma local tissue, the articular cavity and various organs.

With respect to a method of measuring a content of glutathione, a content of oxidative or reductive glutathione is directly measured biochemically by an enzymatic recycling method [refer to Protocol of Active Enzyme Experiments (Saibo Kogaku, separate volume), Shujunsha, pp. 84-88, 1994, Analytical Chemistry, vol. 106, pp. 207-212, 1980, and Cellular Immunology, vol. 164, pp. 73-80, 1995]. Each of these publications is incorporated herein by reference. Further, it can indirectly be measured using a monoclonal antibody or a polyclonal antibody specific to oxidative or reductive macrophages or using a reagent which is specifically reacted with GSH to form a complex and emits fluorescent light through laser excitation, such as monochlorobimane.

Glutathione in the present invention is also called L-glutamyl-L-cysteinylglycine. It is an SH compound which is mostly present in vivo, and generally referred to as "GSH". Glutathione is classified into reductive glutathione and oxidative glutathione. Reductive glutathione refers to the above-mentioned glutathione (GSH). Oxidative glutathione is also called glutathione disulfide, and is referred to as "GSSG".

The macrophage in the present invention also includes the above-mentioned monocyte. Macrophage-related cells called dendritic cells and Kupffer cells are also included. The macrophage is known to secrete or release various mediators such as cytokines and inflammatory mediators from cells thereof. Whether they are secreted or not is determined depending on its activated or differentiated condition, and the amount released varies depending thereon. In the present invention, an attention is directed to the contents of oxidative glutathione and reductive glutathione in macrophages. Macrophages are monitored by the ratio of oxidative macrophages and reductive macrophages, and the immunological state is identified. The balance of these macrophages is modulated with the immunomodulator and the like of the present invention to improve the in vivo immunological state and to treat or prevent various diseases usefully.

In the reductive macrophage, the content of reductive glutathione is relatively higher than that in oxidative macrophage. In the oxidative macrophage, the content of reductive glutathione is relatively lower than that in reductive macrophage. Further, the reductive macrophage and the oxidative macrophage are different in activation of a transcriptional factors due to the difference in the reductive GSH content. Consequently, there occurs a difference in the gene expression of cytokines or inflammatory mediators, so that the type and the amount of the resulting inflammatory cytokines or inflammatory mediators are changed and the quality of inflammation is changed.

With the oxidative macrophage, inflammatory cytokines and mediators such as IL-6, IL-1, IL-8, IL-10, TNF, hydrogen peroxide, superoxide and PGE2 are produced. With the reductive macrophage, nitrogen monoxide (NO), IL-12 and LTB4 are produced. Further, the oxidative macrophage and the reductive macrophage are inter-converted through stimulation or the like. The reductive macrophage can be converted to the oxidative macrophage through artificial stimulation using LPS or PMA inducing inflammatory or ischemic shock and cytokines such as IL-4 and TGFβ. On the contrary, the oxidative macrophage can be converted to the reductive macrophage with the addition of IFNγ, IL-2, lentinan (LNT) which is an antitumor polysaccharide, or lipoic acid with an antioxidant nature. This can be applied to therapy of immunological diseases.

The amounts of the oxidative macrophage and the reductive macrophage vary depending on the pathological state of the said diseases. The amount of the oxidative macrophage contained in the body fluid or the cell sample collected from patients suffering from allergic diseases or advanced cancers is relatively larger than that in the healthy person. This can be used in the examination for diagnosis of immunological diseases and tumor cachexia and the subsequent therapy thereof.

Further, it has been clarified through image analysis using an adherent cell analyzing system (ACAS) or biochemical determination using an enzyme recycling method that a content of reductive glutathione in macrophages harvested from model animals suffering from gastrointestinal inflammatory diseases (hepatitis, Crohn disease and ulcerative colitis) is relatively lower than that in normal animals. This indicates that macrophages are inclined to be oxidative in intestinal inflammatory bowel diseases or gastrointestinal inflammatory diseases, and that oxidative macrophages participate in a mechanism of preventing the progression of diseases. When oxidative macrophages participate in the disease progression, these have to be converted to reductive ones. When oxidative macrophages participate as a defense mechanism of preventing disease progression, the oxidative state of macrophages has to be maintained through administration of a drug. The inventors have assiduously conducted studies as to which of these two possibilities is the essence of diseases. Consequently, they have found for the first time in the world that the oxidative macrophages have the defense mechanism of preventing the progression of chronic inflammatory diseases and autoimmune organ specific inflammatory diseases mainly in the digestive tract, and that it is useful to reduce the content of reductive glutathione in the macrophages as an approach of improving and treating the gastrointestinal inflammatory diseases.

In accordance with the present invention, the low molecular weight compound which has an activity of changing the content of reductive glutathione in the macrophage cell after measuring the same by the above-mentioned method and which maintains the activity even through the oral intake is formulated into a drug in a usual manner, and this drug can be taken in the patient every day or at fixed intervals upon monitoring the condition of the disease. At the chronic stage, the marked effect is brought forth by the long-term administration.

With respect to the definition of the oxidative macrophage and the reductive macrophage in the present invention, the reductive glutathione (GSH) content in the cell is determined through the reaction with monochlorobimane which is a chemical reagent specific to GSH. The macrophage of which the GSH content is increased in comparison with the resident macrophage is defined as the reductive macrophage, while the macrophage of which the GSH content is decreased is defined as the oxidative macrophage. Preferably, the macrophage of which the GSH content is more than 2 nmoles/$5\times10^5$ macrophages by being brought into contact with the low-molecular weight substance capable of oral intake for from 2 to 24 hours is defined as the reductive macrophage, and the macrophage of which the GSH content is less than 0.1 nmoles/$5\times10^5$ macrophages is defined as the oxidative macrophage. Alternatively, the macrophage of which the GSH content is at least twice that of the resident macrophage is defined as the reductive macrophage, while the macrophage of which the GSH content is at most ⅕ that of the resident macrophage is defined as the oxidative macrophage.

As the substance having the activity of changing the content of reductive glutathione in macrophages, any substance will do if macrophages (or monocytes) are incubated at concentrations of $5\times10^5$ cells/200 μl/well using a 96-well microplate, from 0.01 μM to 5 mM of a substance to be tested are added thereto and incubated at 37° C. in a 5% $CO_2$ incubator and the reductive GSH content is increased or decreased relative to the control group after from 2 to 24 hours. A substance that can increase the GSH content to 2 nmoles/$5\times10^5$ macrophages or more or decrease the same to 0.1 nmoles/$5\times10^5$ macrophages or less is preferable. Examples thereof include antioxidants, for example, a precursor of GSH which is metabolized into GSH in cells, such as N-acetylcysteine (NAC), -glutamylcysteine diethyl ester, glutathione derivatives such as glutathione monoester and glutathione diester, lipoic acid and derivatives thereof, ortene, and flavonoid and derivatives thereof. They are substances having an activity of changing the content of glutathione in cells by the incubation with macrophages in vitro for a few hours. These agents can be used either singly or in combination. The effect thereof can be measured by collecting monocytes from an body fluid of local inflammatory sites or a peripheral blood after the intake or the administration and determining the change in the content of reductive glutathione in cells relative to that before the treatment by the above-mentioned method. The usefulness as the immunomodulator is clearly evaluated by this procedure, and the agents are effective for the treatment of the patients. When a cysteine derivative is used as an immunosuppressant, it is included by the above-stated immunomodulator and as a matter of course, it can be used in the same way as stated above.

The diseases to which the present invention is applied include cachectic conditions of patients suffering from cancers; autoimmune diseases such as diabetes, chronic rheumatoid arthritis, SLE and pulmonary fibrosis; inflammatory diseases such as hepatitis, hepatic cirrhosis and inflammatory bowel diseases, centering on gastrointestinal inflammatory diseases; and allergic diseases such as hypersensitive interstitial pneumonia, asthma, atopic cutaneous inflammatory diseases, sarcoidosis, etc.

Especially, as diseases to which the immunosuppressant according to the present invention is applicable, it is expected that it is effective against autoimmune inflammatory diseases. Above all, it is desirable to apply the immunosuppressant to chronic inflammatory diseases caused in digestive organs, including a group of diseases called inflammatory gastrointestinal diseases such as hepatitis, hepatic cirrhosis and inflammatory bowel diseases such as ulcerative colitis and Crohn disease.

The agents can widely be applied to diseases associated with the abnormal Th1/Th2 balance or the functional deficiency of macrophages, for example, cachexia of patents suffering from cancers, diabetes, chronic rheumatoid arthritis, autoimmunological diseases such as SLE, chronic inflammatory diseases such as hepatitis, hepatic cirrhosis, inflammatory bowel diseases, and allergic diseases such as asthma, cutaneous atopy and sarcoidosis. The agents are also effective for chemoprevention of cancers as the immunomodulator. This makes it clear that during the period in which one normal cell undergoes transformation and carcinogenesis in the human body and then reaches to $10^9$ cells where the presence of cancer tissues is clinically detected, the cancerous tissue is profitably present in the reductive condition. That is, it is scientifically verified that active oxygen or the like which is produced by inflammatory responses in vivo contributes to malignant progression.

The immunomodulator used in the present invention can be administered singly in the actual medical care. The immunomodulators capable of oral intake which are included in present invention can also be used in combination. Further, immunomodulator of the present invention can be mixed with, or used in combination with, the other immunomodulator in capable of oral intake but charging the content of reductive glutathione in macrophages with the different function, for example, exogenous and endogenous substances such as β(1-3) glucan typified by lentinan and cytokines typified by interleukin 2(IL-2). Especially when it is required to increase cellular immunity, IL-2 or γ-interferon (γIFN) is used in combination whereby interleukin 12 (IL-12) is produced in vivo in a large amount from the reductive macrophage to more increase the effect the present invention. On the other hand, when the therapeutic effect is intended by decreasing cellular immunity, production of IL-12 is decreased with the combined use of interleukin 4 (IL-4) or TGFβ to increase the effect. It has been found in the present invention that these cytokines change themselves the content of reductive glutathione in macrophages, increasing the usefulness and the scope of the present invention.

When substances which inhibit the production or the function of IL-12, other than antibodies, are used in combination as in vitro substances, a synergistic effect is further expected.

It is also included in the present invention that either of the macrophages which are different in the content of reductive glutathione in cells, namely, the macrophage (oxidative macrophage) having the low reductive GSH content and macrophage (reductive macrophage) having the high reductive GSH content is selectively removed. The substance used in this case may be a low-molecular weight compound or a high-molecular hat compound. Among others, antibodies and derivatives thereof are effective.

As already stated, the correspondence of a variety of functions of macrophages/monocytes to their subsets has been to date totally unknown. Accordingly, although macrophages/monocytes play quite an important role in the triggering and the progression of inflammatory diseases, allergic diseases and immunological diseases, the functional classification on the basis of the presence of distinct macrophage/monocyte sub-sets has not been applied at all to the therapy, improvement and prevention of human diseases, and this application has not been even imagined. Before the completion the present invention, the reductive GSH content of the macrophage was measured, and it was discovered for the first that there is a great difference in an effect of macrophages having different GSH contents on the immunological functions. Further, the contents of oxidative glutathione and reductive glutathione in macrophages which play an important role in the inflammatory reaction were measured to classify heterogeneous macrophages into the two types, namely, oxidative macrophages and reductive macrophages. Then, it was found that the oxidative macrophages induce local chronic inflammatory diseases or allergic reaction accompanied by immunological diseases, that the Th1/Th2 balance controlling the balance of humoral immunity and cellular immunity is regulated by the redox state of macrophages, end that the redox state of the macrophages plays an important role in the progression of immunological diseases. In order to artificially control the presence ratio of these two macrophages, the above-mentioned low-molecular weight substance capable of oral intake is used as a drug, and the selective removal of either of these macrophages is also quite useful. This is also understandable from the fact that various monoclonal antibodies to lymphocytes are on the market as an immunosuppressor. It is easily conceivable to those skilled in the art that antibodies to either of these macrophages or to markers expressed in larger amounts in either of these macrophages can be used.

Further, substances having toxicity to cells or derivatives thereof can be used. However, since there is a great difference in intracellular enzymatic activities between reductive macrophages and oxidative macrophages, substances which can be converted to those having a selective cytotoxicity within either of reductive macrophages or oxidative macrophages are most appropriate prodrugs in the present invention. For example, the use of a pyrimidine nucleotide phosphorylase enzymatic activity or a glutathione-S-transferase enzymatic activity which is increased in the oxidative macrophages is mentioned. There is a product in which an alkylating agent having a cytotoxicity is conjugated with glutathione.

That the immunomodulator of the present invention can be applied to a wide variety of immunological diseases is clearly seen from the fact that it controls the secretion of an inflammatory mediator from macrophages at the very beginning stage of the production. For example, non-steroidal acidic anti-inflammatory drug (aspirin or the like) is said to exhibit the pharmaceutical effect by controlling production or secretion of prostaglandin. Meanwhile, an antioxidant such as vitamin E exhibits the pharmaceutical effect by controlling production of active oxygen. Thus, the function is only to control one of various properties of macrophages which are inflammatory cells. For this reason, its effect is not workable, and almost no effect is exhibited to chronic inflammatory diseases in particular. On the other hand, the immunomodulator of the present invention controls the redox condition of macrophages, and can suppress the production of a large number of harmful inflammatory mediators all at once. In this context, the conventional concept to date of anti-inflammatory drugs is said to be fundamentally changed.

As stated above, the useful pharmaceutical effect of the immunomodulator of the present invention in the actual medical care is self-evident from its profitable immunological activity. It is useful for both the acute and chronic stages of diseases. Especially, it can widely be applied to diseases associated with the abnormal Th1/Th2 balance or the functional deficiency or the abnormality of macrophages, for example, cachexia of patients suffering from cancers; autoimmunological diseases such as diabetes, chronic rheumatoid arthritis, SLE and pulmonary fibrosis; chronic inflammatory diseases such as hepatitis, hepatic cirrhosis and gastrointestinal inflammatory diseases centering on inflammatory bowel diseases (ulcerative colitis and Crohn disease); and allergic diseases such as hypersensitive interstitial pneumonia, asthma, cutaneous atopy and sarcoidosis. It is also effective for chemoprevention of cancers. With respect to the cachectic condition of patients suffering from cancers, an effect to increase the survival rate is expected, and the immunomodulator is considered to be also useful especially in the improvement of quality of life (QOL) of the patient.

Especially, with respect to the immunomodulator of the invention, the use of the cystine derivatives as an immunosuppressant is described in detail below.

The substances having the activity of reducing the content of reductive glutathione are as mentioned above. The cystine derivatives represented by the structural formula (1) and having the activity of reducing the content of reductive glutathione in the macrophages are all included in the cystine derivatives used in the invention. Examples thereof include N,N'-diacetylcystine-[(NAC)$_2$], N,N'-dipropylcystine [(NPC)$_2$], N,N'-diacetylcystinedimethyl ester [(NAC-OMe)$_2$], N,N'-diacetylcystinediisopropyl ester [(NAC-OiPr)$_2$] and N,N'-di-L-alanylcystinedimethyl ester [(NAlaC-OMe)$_2$.

With respect to $R^1$ and $R^2$ in the structure of the compounds, a wide variety of substituents can be used so long as reductive glutathione in the macrophages is oxidized into oxidative macrophages through the disulfide linkage. For example, $R^1$ and $R^2$, independently from each other, represent an alkyl group having from 1 to 12 carbon atoms (inclusive of all specific values and subranges therebetween, 1, 2, 3, 4, 5, 6, 7, 8, 9, 10 and 11 carbon atoms) or a substituted alkyl group such as the nitroxybutyl group, and $R^3$ and $R^4$, independently from each other, represent an acyl group having from 1 to 12 carbon atoms (inclusive of all specific values and subranges therebetween, 1, 2, 3, 4, 5, 6, 7, 8, 9, 10 and 11 carbon atoms) or a peptidyl group. The peptidyl group means an amino acid residue or peptide residue consisting of plural amino acids, which is bound through its carboxyl group. The number of amino acid may vary widely, for example, from 1 to 10 amino acids. Preferably, the acyl groups are derived from hydrocarbon carboxylic acids.

These agents can be used either singly or in combination. The effect thereof can be estimated by harvesting monocytes from inflammatory parts or peripheral blood after intake or administration, examining the change in the content of reductive glutathione in cells relative to that before treatment using the method and measuring the change in the immunological activity in vivo. This clearly proves the usefulness as the immunosuppressant in particular, and these agents are effective against diseases.

The administration form is not particularly limited, and it includes administration by injection and oral administration.

However, the oral administration is advantageous. The dose of the substance having an activity of changing the content of reductive glutathione as an active ingredient is selected depending on the conditions of patients or the like to which the substance is administered or the use purpose. In the case of patients suffering from serious diseases, for example, a advanced gastric cancer, the dose is between 1 and 5,000 mg (oral drug), preferably between 10 and 500 mg/day. It is not particularly difficult to produce preparations, and preparations can be produced in the form of an oral agent, an injection, a percutaneous agent and the like as required in a usual manner.

It has been described above that the immunomodulator of the present invention is quite useful and quite new as a drug im a narrow sense. Since the immunomodulator of the present invention contains a substance capable of oral intake as a main ingredient, its use is not limited to drugs in the actual medical care. That is, the immunomodulator of the present invention can also be provided in the form of a food (including all that are put into the mouth, such as a chewing gum, a tooth paste the like), as a food for medical care, a health food or a special sanitary food containing a substance having an activity of changing the content of reductive glutathione in human macrophages (including monocytes, Kupffer cells and dendritic cells) either singly or as a mixture, as well as in the form of a nutrient an infusion. These are also included in the present invention. It can also be contained in a liquid component or take the form of a solid food.

The food, the nutrient and the infusion can be applied to the same diseases as those to which the drugs are applied.

The immunomodulator of the present invention can be provided in the form of the food, the nutrient and the infusion having an immunomodulatory function for improvement of the cachectic condition of patients suffering from cancers, diabetes, inflammatory bowel diseases, chronic rheumatoid arthritis, hepatitis, hepatic cirrhosis, gastrointestinal inflammatory diseases centering on inflammatory bowel diseases (ulcerative colitis and Crohn disease), autoimmune inflammatory diseases, and for chemoprevention of cancer. The dose of the active ingredient may be determined according to what has been described in the above-mentioned drugs. It can be applied not only to patients suffering from attacked or chronic diseases but also to high-risk persons suffering from adult diseases or the like.

Having generally described this invention, a further understanding can be obtained by reference to certain specific examples which are provided herein for purposes of illustration only and are not intended to be limiting unless otherwise specified.

EXAMPLES

Example 1

Test for Functions of Oxidative Macrophages and Reductive Macrophages

Oxidative macrophages were induced by administering 20 μg of LPS (lipopolysaccharide) to an abdominal cavity of a mouse, and reductive macrophages were induced by administering 100 μg of lentinan to an abdominal cavity of a mouse three times every two days. These were clarified by adhering peritoneal exudate cells to the plastic surface, then reacting the same with 10 μM of monochlorobimane at 37° C. for 30 minutes and conducting analysis with Adherent Cell Analyzing System (ACAS). The increase in the amounts of oxidative macrophages can easily be measured visually from the fact that almost no reaction product is observed, that is, gray or blue image is obtained, and the increase in the amounts of reductive macrophages from the fact that the red or yellow image is obtained, respectively.

Accordingly, NO, IL-6 and PGE2 produced by inducing the peritoneal exudate cells into oxidative end reductive cells were measured.

(1) Materials

Cells: The peritoneal exudate cells obtained by the above-mentioned stimulation, namely, the macrophages were added to a 96-well microplate in an amount of $1 \times 10^5$ cells/200 μl each.

Medium: Phenol red-free RPM 11640: 200 μl/well

LPS: Lipopolysaccharide (made by Sigma Co.) (origin: *E. coli*) 100 ng/ml

IFNγ: 100 units/ml (2) Incubation

Incubated in a 5% $CO_2$ incubator at 37° C. for 48 hours.

(3) Measuring Method

After the completion of the above-mentioned incubation, the culture supernatant was recovered. The amount of IL-6 was measured by the proliferation assay using an IL-6-dependent cell strain, MH60, the amount of PGE2 was measured using an ELISA-kit, and the amount of NO was measured using a Griess-Romijn reagent. These measurements were conducted by a method which those skilled in the art usually employ.

Figure 3:
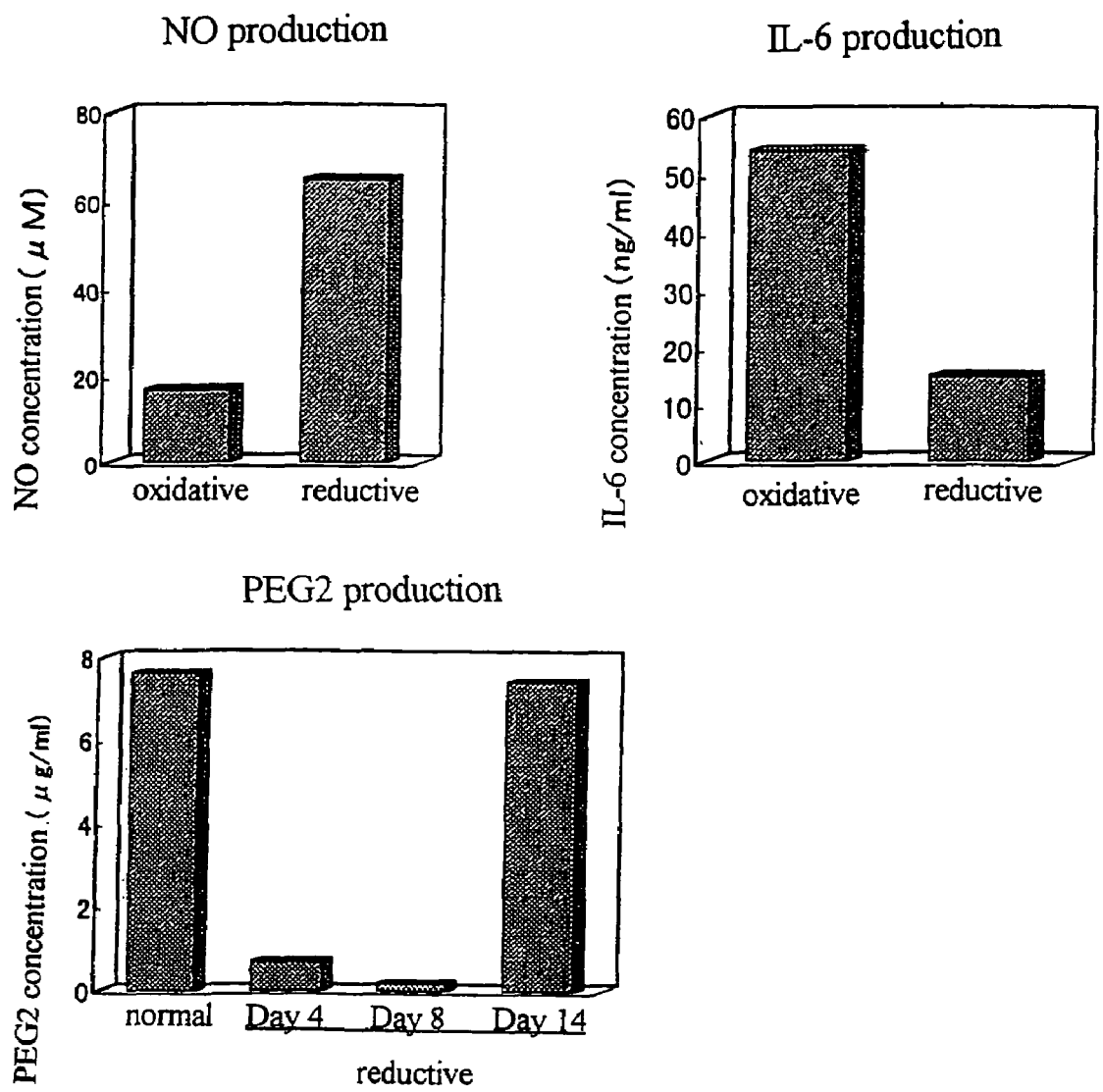
FIG. 3 is a view showing the results of the examination of functions of both macrophages, namely the functional differences between oxidative macrophages and reductive macrophages.

(4) Results:

The results are shown in FIG. 3. As is clear from FIG. 3, there are differences in the concentration and the type among inflammatory cytokine IL-6, inflammatory mediator PGE2 and NO produced between oxidative macrophages and reductive macrophages. That is, with the oxidative macrophages, the production of IL-6, a Th2 cytokine and the production of PGE2, which is immunosuppressive to suppress the Th1 induction are increased, and the production of NO is decreased. On the contrary, with the reductive macrophages, the production of NO is increased, and the production of PGE2 and the production of IL-6 are suppressed. Thus, there is a functional difference seen between both macrophages.

Example 2

Test Using Animal Disease Models which are Immunologically Deficient by Knocking Out a Gene In order to clarify a mechanism underlying the conversion of an acute to a chronic phase and progression of inflammatory diseases, it is important to analyze molecularly why there is a difference in the production of an inflammatory mediator or a cytokine between oxidative MΦ and reductive MΦ. Generally, extracellular stimulation (ligand or the like) of the all is signaled into cells through a receptor present on the cell surface. Various kinases are activated with signals from the receptor, and transcriptional factors are also activated in cytoplasm. The activated transcriptional factors are translocated into the nucleus, and bound to target genes to conduct gene expression. According to the recent studies, it is being clarified that the intracellular redox system regulates activation of transcriptional factors, translocation thereof into the nucleus and binding with genes (Annual Rev. Immunology, vol. 8, pp. 453-475, 1990, Embo J., 10, 2247-2251, 1991). It is currently unknown how the intracellular redox system participates in the gene expression system after the receptor triggering in MΦ. As a method of clarifying the same, MΦ was harvested from a knock out mouse deficient in a molecule participating in a signal transduction system from a receptor, and the function of the redox state was analyzed. Specifically, a common γ chain (γc) which is commonly used as a receptor constituting molecule of IL-2, IL-4, IL-7, IL-9 and IL-5 and Jak3 which is a molecule present downstream thereof and transducing a signal from γc were used as target molecules.

Cytokine and Stimulator:

As mouse IFNγ, a recombinant supplied by Genzyme was used. As human IL-2 and human IL-6, recombinants supplied by Ajinomoto Co., Inc. were used. As human IL-12, a recombinant supplied by Pharmingen was used.

As LPS, a substance derived from *E. coli* 055:B5 supplied by Difco was used. As lentinan, a preparation produced by Ajinomoto Co., Inc. was used.

Mice Used:

γc Knock out mice were obtained from Professor Sugamura, Tohoku University Medical School. Jak3 knock out mice were obtained from Professor Saito, Chiba University Medical School.

As wild mice used for mating and as a control, C57BL/6 obtained from Charles River Japan (CRJ) was used.

Harvest of Peritoneal MΦ:

Peritoneal cells were harvested by injecting 5 ml of a phenol red-free DMEM medium (supplied by Nikken Seibutsusha) ice-cooled into a peritoneal cavity of a mouse which had been put to sacrificial death with ether using an injection cylinder fitted with a 22-gauge needle, squeezing the same and pulling out the medium.

Determination of the Amount of IL-6:

A stimulator was added to $1 \times 10^6$ MΦ, and the incubation was conducted at 37° C. for 2 days in a $CO_2$ incubator. After centrifugation, the culture supernatant was collected.

The amount of IL-6 was determined using IL-6 dependent mouse hybridoma MH60 cells (J. Eur. Immunol., vol. 18, p. 951, 1988). One hundred microliters of the culture supernatant were added to 100 μl of the MH60 cell suspension adjusted to $1 \times 10^5$ cells/ml in a 10% FCS-containing RPMI medium, and the mixed solution was incubated at 37° C. for 2 days in a $CO_2$ incubator. Subsequently, 10 μl of MTT (supplied by Sigma Co.) solution adjusted to a concentration of 5 mg/ml in the same medium were added thereto, and the reaction was conducted at 37° C. for 5 hours. After the completion of the reaction, the centrifugation was conducted. The supernatant (160 μl) was removed, and 100 μl of a mixture of hydrochloric acid and propanol were added to the residue. The suspension was conducted using a pipetman to dissolve the cells. Immediately after the dissolution, an absorbance of 570 nm was measured with an immunometer (supplied by Bio-Rad).

Measurement of a Concentration of $NO_2$:

A stimulator was added to $1 \times 10^5$ MΦ, and the incubation was conducted at 37° C. for 2 days in a $CO_2$ incubator. After the completion of the centrifugation, the culture supernatant was collected.

One hundred microliters of a Griess-Romijn reagent (supplied by Waco Pure Chemical Industries, Ltd.) adjusted to a concentration of 50 mg/ml in distilled water were added to 100 μl of the culture supernatant, and the reaction was conducted at room temperature for 15 minutes. After the completion of reaction, an absorbance of 540 nm was measured. $NaNO_2$ was used as a standard.

Determination of GSH in Cells with ACAS:

Three-hundred microliters of a cell suspension adjusted concentration of $3 \times 10^5$ cells/ml in an RPMI 1640 medium (phenol red-free) were charged into a chambered coverglass (#136439, supplied by Nunc), and incubated at 37° C. for 2 hours using a $CO_2$ incubator. The culture solution was washed with the medium, and 300 μl of monochlorobimane (supplied by Molecular Plobe) adjusted to 10 μM in the same medium were added thereto. The mixture was charged into a $CO_2$ incubator of 37° C., and the reaction was conducted for 30 minutes. The fluorescent intensity was measured with ACAS. In ACAS, a UV laser was used.

Determination of an Amount of IL-12:

The amount of IL-12 was determined through bioassay using cells of human T cell strain 2D6 (J. Leukocyte Biology, vol. 61, p. 346, 1997).

2D6 cells which had been incubated in an RPMI 1640 medium containing 500 pg/ml of recombinant human IL-12, 50 μM of 2-mercaptoethanol and 10% FCS (fetal calf serum) were moved to a tube, and centrifugally washed three times with the above-mentioned medium without IL-12 and cell density was adjusted to $1 \times 10^5$/ml. The cell suspension was added in an amount of 100 μl each to a 96-well flat bottom plate containing a sample serially diluted in advance with an RPMI 1640 medium containing 50 μM of 2-mercaptoethanol and 10% FCS in an amount of 100 μl each. Subsequently, the mixture was charged into a 5% $O_2$ incubator of 37° C., and incubated for 48 hours. For final 6 hours, $^3$H-TdR was pulsed (a substance adjusted to 370 kBq/ml in an RPMI 1640 medium containing 50 μM of 2-mercaptoethanol and 10% FCS was added in an amount of 50 μl each). The cells a harvested, and the radioactivity was measured using a β counter (Matrix 96, supplied by Packard).

Measurement of the GSH Content in MΦ Produced from Knock Out Mice:

Peritoneal cells were produced from knock out mice, and the GSH content in cells was analyzed by ACAS using an MCB reagent. The content of reductive glutathione was clearly decreased in any mice compared with control mice (C57BL/6).

Function of MΦ Produced from Knock Out Mice:

Peritoneal cells were produced from wild mice (C57BL/6) knock out mice, and stimulated with LPS, IL-2, IFNγ and a combination thereof. The NO production, the IL-6 production the IL-12 production were measured. Almost no NO production was observed in any mice derived MΦ in the absence of stimulation. In the stimulation with the combination of LPS IFNγ, almost no additive effect was observed in the γc knock out mice, and the NO production was decreased to less than half that in control mice. The same results as in γc were provided in Jak3 knock out mice. Further, the IL-6 production was analyzed. In the LPS stimulation, an increase in the IL-6 production was observed in γc knock out mice (962 pg/ml relative to 81 pg/ml of a control). In the IFNγ stimulation, an increase in the IL-6 production was observed in γc knock out mice. The results were the same with the suppression pattern of the NO production. Still further, the IL-12 production with the LPS stimulation and the IFNγ stimulation was examined. No production was observed at all in any mice derived MΦ. This proves that in the sick animals of the gene knock out mice used herein, the amount of the oxidative macrophages is increased to increase the humoral immunity or the allergic reaction mainly caused by Th2 and to decrease the cellular immunity supported by Th1. In the animal disease models, it is clearly shown that the diagnosis of immunological diseases required for the immunomodulator of the present invention is original and significant.

Example 3

Determination of the Amount of Reductive Glutathione in MΦ of Advanced Tumor-bearing Mice Method:

Oxidative and reductive macrophages collected from peritoneal cavities of advanced tumor-bearing cachectic mice (COLON 26) and normal mice were determined. The COLON 26 transplantable tumor well known to induce a cancer cachexia was implanted subcutaneously in the back portion of CDF1 mice at a density of $5 \times 10^5$ cells/mouse. On day 21 after the tumor implantation, the cachectic condition was provided. Five milliliters of a physiological saline solution were intraperitoneally injected into the mice which became resistant to a therapeutic treatment. Peritoneal macrophages were collected, and suspended in a phenol red-free RPMI 1640 medium containing 10% fetal calf serum to a density of $3 \times 10^5$ cells/ml. One hundred microliters of the suspension were charged in a Lab-Tek Chamber Slide (#136439, supplied by Nunc), and incubated in 5% $CO_2$ at 37° C. for 3 hours. After the nonadherent cells were removed, 200 μl of the above-mentioned medium free from serum were added thereto, and monochlorobimane (MCB) was added thereto in an amount of 10 μM. The reaction was conducted for 30 minutes, and the image analysis was conducted on the basis of the UV absorption using an ACAS device (supplied by Meridien).

Results:

The content of reductive glutathione was determined by ACAS. As a result, in the advanced tumor-bearing mice, the amount of the macrophage of which the reductive glutathione content was decreased, namely, the oxidative macrophage was relatively increased in comparison with that in the normal mice. Since the amount of the oxidative macrophage was increased, the amount of IL-6 in the above-mentioned macrophage culture supernatant was markedly increased (600 pg/ml relative to 120 pg/ml in control mice). Further, the amount of PGE 2 was 32 ng/ml relative to 7.6 ng/ml in control mice, and it was increased tp 5 times or more. It was found that the immunosuppressive state or the cachectic state at the advanced tumor-bearing stage is based on the excessive production of these mediators. In addition, the increase in an amount of active oxygen produced was also observed. It shows that the redox state of macrophages is measured upon determination of the glutathione content without measuring a large number of parameters whereby the examination for diagnosis of the pathological state and the immunological function of patients suffering from cancers can be conducted easily and exactly. Accordingly, the above-mentioned classification of macrophages enables the examination for diagnosis of diseases and the immunological function of patients suffering from cancers.

Example 4

Induction of Reductive Macrophages by Oral Administration of Glutathione Ethyl Ester to Advanced Tumor-bearing Mice The COLON 26 transplantable tumor was implanted subcutaneously in the back portion of CDF1 mice at a density of $5 \times 10^5$ cells/mouse. On day 21 after the tumor implantation, the mice were proved to be in the cachectic condition. Glutathione ethyl ester was orally administered to the mice every day in a dosage of 1 mg/0.5 ml/h. This oral administration was continued for 10 days. The peritoneal cells were collected from the mice in the same manner as in Example 3. Peritoneal macrophages were collected, and suspended in a phenol red-free RPMI 1640 medium containing 10% fetal calf serum to a density $3 \times 10^5$ cells/ml. The suspension was charged into a Lab-Tek Chamber Slide (#136439, supplied by Nunc) in an amount of 100 µl, and the incubation was conducted in 5% $CO_2$ at 37° C. for 3 hours. After the nonadherent cells were removed, 200 µl of above-mentioned medium free from serum were added thereto, and 10 µM of monochlorobimane were then added thereto. The reaction was conducted for 30 minutes, and the image analysis was conducted based on the UV absorption using an ACAS device (supplied by Meridien).

Results:

The content of reductive glutathione was determined by ACAS method. Consequently, in the advanced tumor-bearing model mice to which glutathione ethyl ester had been administered, the amount of the macrophage of which the reductive glutathione content was decreased, namely, the oxidative macrophage was relatively decreased in comparison with that in control mice to which the physiological saline solution had been administered. Since the amount of the reductive macrophage was increased, the amount of IL-6 in the above-mentioned macrophage culture supernatant was decreased (642 pg/ml relative to 5,200 pg/ml in control mice). Further, the amount of PGE2 was also much decreased to 6.5 ng/ml relative to 32 ng/ml in control mice. It was thus clarified that the immunosuppressive state or the cachectic state at the advanced tumor-bearing stage can be improved by the oral administration of glutathione ethyl ester. Accordingly, the average number of survival days of mice in the treated group increased from 42 (in control mice) to 148.

Example 5

Examination of Macrophages Collected from the Patient Suffering from Sarcoidosis and Conversion of Oxidative Macrophages to Reductive Macrophages The amounts of oxidative and reductive monocytes macrophages contained in monocytes preparation separated and collected in a usual manner from the peripheral blood and the thoracic cavity of the patient suffering from sarcoidosis were examined by biochemically measuring the contents of reductive glutathione (GSH) end oxidative glutathione (GSSG) by the enzyme recycling method. The peripheral blood of the healthy person was used as a control.

Materials:

The peripheral blood of the healthy person and the peripheral blood of the patient suffering from sarcoidosis were collected with heparin. Or 150 ml of a physiological saline solution was injected into the bronchia of the patient using a bronchofiber, and 75 ml of bronchoalveolar lavaged fluid were recovered. Monocytes obtained by separating and purifying both of them using Ficoll-Hypaque (LYMPHOPREP) were suspended in an RPMI 1640 medium containing 10% fetal calf serum, and washed three times to obtain macrophage/monocyte preparation adherent to a glass petri dish for 30 minutes. Subsequently, a group incubated for 3 hours with the addition of 5 mM N-acetylcysteine (NAC) and a group of a medium component alone were prepared. A rubber policeman was used to recover adherent cells from the petri dish. With respect to $5 \times 10^5$ macrophages, the following examination was conducted.

Method:

The contents of reductive glutathione and oxidative glutathione were measured by the above-mentioned enzyme recycling method.

Production of Samples:

One hundred microliters of Triton X-100 prepared with a 0.1 M phosphate buffer (pH 7.5) containing 5 mM EDTA ice-cooled were added to cell pellets which had been washed with PBS, and the mixture was allowed to stand at room temperature for 5 minutes to dissolve the cells. Fifteen microliters of 0.1 M HCl were added thereto, and 15 µl of a 50% sulfosalicylic acid (SSA) solution were further added thereto. The mixture was centrifuged at 12,000 rpm for 5 minutes, and the supernatant was collected [*] to form a measuring sample having a total glutathione concentration (GSH+GSSG).

Measuring Method:

A 10 mM phosphate buffer (590 µl, pH 7.5) containing 0.5 mM EDTA, 100 µl of glutathione reductase (supplied by Boehlinger Mannhein) adjusted to a concentration of 6 u/ml in the same buffer, 50 µl of 4 mM NADPH (supplied by Sigma Co.) prepared with 5% $NaHCO_3$ and 10 µl of the sample were mixed. The mixture was incubated at 37° C. for 5 minutes. Fifty microliters of a 10 mM 5,5'-dithio-bis(2-nitrobenzoic acid) (DTNB, supplied by Sigma Co.) prepared with a 0.1 M phosphate buffer (pH 7.5) containing 5 mM EDTA were added thereto. The change in the absorbance of 412 nm at 37° C. over the course of time was measured using a spectrophotometer. As a standard sample, GSH (supplied Sigma Co.) prepared in the same manner as the above-mentioned sample was used. Separately, the content of oxidative glutathione (GSSG) alone was measured,—2 µl of 2-vinylpyridine (supplied by Tokyo Kaseisha) were added thereto after the above-mentioned procedure [*] and were mixed at room temperature for 1 minute, and after the pH was adjusted to 7.5, reaction mixture was allowed to stand at room temperature 60 minutes to form a measuring sample, and the measurement conducted in the above-mentioned manner.—and the content of reductive glutathione (GSH) was obtained by the subtraction from the total glutathione content.

Results:

With respect to the contents of reductive glutathione and oxidative glutathione in the peripheral blood of the patient, the GSSG content was 5.29 µM, and the GSH content was 20.45 µM. Thus, the ratio of reductive GSH was approximately 80%, and still higher (the ratio of reductive GSH was 90% or more in the healthy person). In the macrophages within the thoracic cavity, the content of reductive GSH was 1.45 µM, and the content of oxidative GSSG was 15.85 µM. Thus, the ratio of oxidative GSSG was approximately 86%, and the presence ratio thereof was completely inverted. In the NAC addition group, content of reductive GSH was 20.45 µM, and the content of oxidative GSSG was 4.32 µM. Thus, the content of oxidative GSSG was largely decreased, and the ratio of reductive GSH exceeded 80%. In this manner, the peripheral blood level was recovered. It shows that in this disease, the oxidative macrophages play a great role in the progression of the disease and this progression can be improved through NAC administration. Thus, the usefulness of the present invention is clarified not only in animal disease models but also in patients suffering from rheumatoid arthritis or diabetes and people with a high risk of these diseases.

Example 6

Induction of Reductive Macrophages by Oral Administration of NAC and GSH-OEt Macrophages (MΦ) were prepared from knock out mice deficient in a molecule participating in a signal transduction system from a receptor, and the function of the redox system was analyzed. Specifically, a common γ chain (γc) which is commonly used as a receptor constituting molecule of IL-2, IL-4, IL-7, IL-9 and IL-15 and JaK3, a molecule present downstream thereof and transducing a signal from γc were gene targeted molecules. Methods applied in Example 2 was repeated. JaK3 knock out mice were divided into three groups. A control group was a group of usual city water free-intake. An NAC group was a group of free intake of city water containing 1 mg/ml of NAC. A GSH-OEt group was a group of free intake of city water containing 1 mg/ml of GSH-OEt. Breeding was continued under SPF condition for 24 days, and peritoneal exudate cells, namely, macrophages were likewise obtained.

Cytokines and Stimulator:

A recombinant supplied by Genzyme was used as mouse IFN. Recombinants supplied by Ajinomoto Co., Inc. were used as human IL-2 and human IL-6. A recombinant supplied by Pharmigen was used as human IL-12.

A product derived from *E. coli.* 055; B5 as supplied by Difco was used as LPS. A preparation supplied by Ajinomoto Co. Inc. was used as lentinan.

Determination of an amount of IL-6:

Measurement of an $NO_2$ concentration:

Determination of a GSH content in cells by ACAS:

Determination of an amount of IL-12:

These were all conducted in the same manner as in Example 2.

Measurement of a GSH Content in MΦ Prepared from Knock Out Mice:

Peritoneal cells of knock out mice which had undergone the respective treatments were harvested, and the GSH content in the cells was analyzed using ACAS with MCB. In any of the mice in the groups of free intake of city waters containing NAC and GSH-OEt, the content of reductive glutathione in MΦ was markedly increased in comparison with that in control mice (city or free intake group). The image of reductive MΦ derived through intraperitoneal administration of NAC in normal mice was shown.

Function of MΦ Harvested from Knock Out Mice:

Peritoneal cells were harvested from three groups of knock out mice, and stimulated with LPS, IL-2, IFNγ and a combination thereof. The NO production, the IL-6 production and the IL-12 production were measured. With respect to the NO production, almost no NO production was observed in any mice derived MΦ in the absence of stimulation. Then, the IL-6 production was analyzed. In LPS stimulation, the amount was detected as 962 pg/ml in the knock out mice derived MΦ culture, 122 pg/ml in the NAC group, and 82 pg/ml in the GSH-OEt group. In view of the function, it was identified that the conversion to reductive macrophages was possible. In consideration of the fact that IL-6 is a main cytokine of inducing Th2, it is clearly shown that the biological Th1/Th2 balance can be controlled by the oral intake of these substances. This result was inversely related with the suppression of the NO production and the recovery pattern with medications. Next, the IL-12 production by stimulation of LPS or IFNγ was examined. No production was observed at all in the control group. This shows that in the animals disease models, the JaK3 gene knock out mice used here, the amount of the oxidative macrophage is increased, humoral immunity or an allergic reaction mainly caused by Th2 is increased, and cellular immunity caused by Th1 is decreased. On the other hand, it was identified that in the NAC and GSH-OEt administration groups, the amounts of IL-12 are 420 pg/ml and 610 pg/ml respectively. This proves that in the animal disease models, the immunomodulator of the present invention is also useful in the improvement of the immunological diseases, and is original and significant.

Example 7

Difference in the IL-12 Production Between Reductive and Oxidative Macrophages When there are defects in differentiation, selection and functional expression steps of T cells, the host immune system becomes deficient. From this fact, it is considered that T cells play an central role in the host immune system. Helper T cells (Th) which are one subset of T cells produce lymphokines to regulate immunocytes or inflammatory cells. Recently, the following concept has been proposed. That is, Th is further classified into two types, Th1 and Th2 depending on the types of the lymphokines produced, and these cells have the different immunological functions (J. Immunol., vol. 136, pp. 2348, 1986). That is, Th1 produces IL-2 or IFNγ, and is a main cell to modulate cellular immunity. Th2 produces IL-4, IL-5, IL-6 and IL-10, and is a main cell to modulate humoral immunity. The homeostasis of the in vivo immunity is maintained by the Th1/Th2 balance. Usually, when the Th1/Th2 balance is inclined to either of Th1 and Th2, the host correspond to correct the skewing and tend to maintain the homeostasis. However, it is considered that when the imbalance is not corrected for some reasons, immunological diseases will occur. Th1 and Th2 are differentiated from the precursor of them, namely Th0. In the differentiation of Th0 to Th1, IL-12 produced by MΦ is important (Immunology Today, vol. 335, p 14, 1993). In the differentiation of Th0 to Th2, IL-4 produced by NKT cells is important (J. Exp. Medicine, vol. 179, pp. 1285, 1994).

In the above-mentioned Example, it is clarified that the MΦ function differs depending on the difference in the redox state of MΦ. With respect to MΦ, there are two types of MΦ, oxidative MΦ and reductive MΦ based on the difference in the GSH content, and these two distinctive MΦ behave differently in the NO or IL-6 production. The main producer of IL-12, which induces differentiation of Th0 to Th1 and which is a key molecule of controlling the Th1/Th2 balance, is considered to be MΦ. However, the detailed analysis has not yet been reported. In view of the clarification of attack mechanism of immunological diseases, it is quite interesting to know whether or not the IL-12 production is different between oxidative MΦ and reductive MΦ. The present inventors have found that IL-12 is produced from only reductive MΦ, and that IL-4 considered to control the Th1/Th2 balance like IL-12 acts on oxidative MΦ and reductive MΦ whereby the Th1/Th 2 balance is skewed to the Th2 side. On the basis of the findings which were obtained prior to the completion of the present invention, it is shown that the redox state of MΦ regulates the Th1/Th2 balance, and the usefulness of the present invention in the diagnosis of immunological diseases is described.

Figure 4:
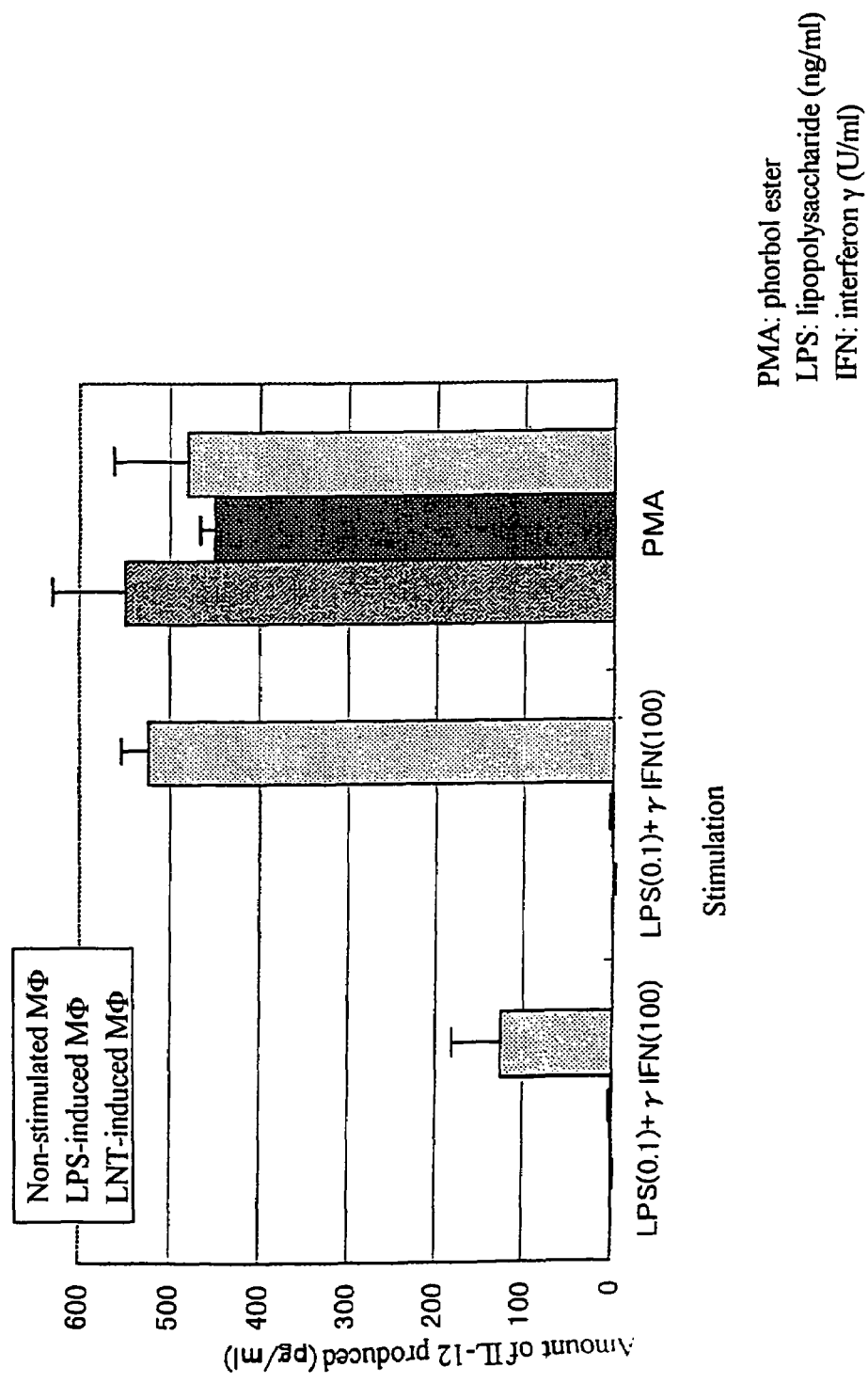
FIG. 4 is a view showing the results of examining whether there is a difference in the IL-12 production between Lentinan (LNT) induced MΦ and Lipopolysaccharide (LPS) induced MΦ. It indicates that there is a great difference in the amount of IL-12 (Th1 inducing cytokine) produced between oxidative and reductive macrophages and IL-12 is produced only from reductive macrophages with the high intracellular reductive glutathione content.

IL-12 is Produced from Reductive MΦ:

In Example 1, it was indicated that MΦ produced by injecting lentinan (LNT) intraperitoneally was reductive MΦ with the high GSH content and that MΦ induced by injecting LPS intraperitoneally was oxidative MΦ with the low GSH content. It was examined whether there is a difference in the IL-12 production between LNT-induced MΦ and LPS-induced MΦ. By stimulation with LPS and INFγ, the remarkable IL-12 production (1,312 pg/ml) was observed in the LNT-induced MΦ. However, no IL-12 production was observed in LPS-induced MΦ and control resident MΦ (FIG. 4). Next, the same analysis was conducted using MΦ induced by intraperitoneally injecting substances for changing the GSH content in cells. With respect to MΦ induced by administering glutathione monoethyl ester (GSH-OEt), a substance increasing the GSH content in cells and diethyl maleate (DEM), a substance decreasing the same, IL-12 (3,570 pg/ml) was produced only in MΦ derived from GSH-OEt administered mice through stimulation with LPS and IFNγ. These results show that IL-12 is produced only by reductive MΦ having the high GSH content in cells.

The IL-12 production from reductive MΦ is suppressed by decreasing the GSH content in cells:

As mentioned above, IL-12 was produced only in reductive MΦ having the high GSH content in cells. It was examined whether this production is suppressed by converting MΦ to oxidative MΦ. That is, it was analyzed whether the IL-12 production is suppressed by exposing lentinan-induced MΦ with DEM. As a result, it was clarified that the IL-12 production (828 pg/ml) from lentinan-induced MΦ is completely suppressed (0 pg/ml) with the addition of DEM. That is, it was suggested that reductive glutathione in cells is deprived through DEM treatment and reductive MΦ is converted to oxidative MΦ to suppress the IL-12 production.

IL-4 Suppresses the IL-12 Production by Reductive MΦ:

IL-4 is a cytokine which acts on MΦ suppressively. IL-4 is considered to have an opposite function to IL-12 in the Th1/Th2 balance as well. Accordingly, it was examined whether IL-4 acts suppressively on the IL-12 production by reductive MΦ. It was clarified that the IL-12 production by LNT-induced MΦ and the IL-12 production by GSH-OEt administered mouse MΦ are remarkably suppressed by the pretreatment with IL-4 (from 1, 580 pg/ml to 370 pg/ml and from 490 pg/ml to 258 pg/ml). That is, it was suggested that there is a possibility that IL-4 acts on MΦ to suppress the IL-12 production whereby the Th1/Th2 balance is skewed to the Th2 side. At this time, it was clarified from the image analysis by ACAS that IL-4 markedly decreases the content of reductive glutathione in MΦ.

IL-4 Suppresses the NO Production and Increases the IL-6 Production:

Reductive MΦ increases the NO production by the IFNγ stimulation in comparison with oxidative MΦ, and rather suppresses the IL-6 production. IFNγ is known to be a cytokine produced from Th1 cells. What function IL-4 shows in the NO production and the IL-6 production with IFNγ was analyzed using respective MΦ's. IFNγ NO production from MΦ pretreated with IL-4 was significantly suppressed in comparison with MΦ untreated with IL-4. Further, MΦ of which the GSH content in cells was increased by the stimulation with GSH-OEt and MΦ of which the GSH content in cells was decreased by the stimulation with DEM were pretreated with IL-4, and IFNγ thereafter and LPS stimulation was carried out to induce NO production. As a result, the NO production was remarkably suppressed in IL-4-treated MΦ in comparison with IL-4-untreated MΦ in both subsets of MΦ.

Meanwhile, with respect to the IL-6 production, the production with IFNγ was markedly increased by pretreatment with IL-4 in resident MΦ, LPS-induced MΦ and LNT-induced MΦ.

Further, MΦ of which the GSH content in cells was increased by the stimulation with GSH-OEt and MΦ of which the GSH content in cells was decreased by the stimulation of DEM were pretreated with IL-4, and IFNγ was exposed thereon to induce the IL-6 production. Consequently, the IL-6 production was increased in IL-4-treated MΦ's in comparison with IL-4-untreated MΦ. These results revealed that IL-4 induces oxidative macrophages by decreasing the content of reductive glutathione in cells, suppressing the NO production by the stimulation with IFNγ and increasing the IL-6 production. This indicates that IL-4 suppresses the NO production by IFNγ, namely, Th1 type response, increases the IL-6 production by IFNγ, and has an activity of enhancing Th2 type response. These findings scientifically prove the usefulness of the immunomodulator according to the present invention.

Example 8

Enhancement of IL-12 Production with a Combination of NAC Orally Taken in and IL-2 Infusion Two groups, namely, a group of 8-week-old DBA/2 female mice which were caused to freely drink city water as in Example 6, and a group of the same female mice which were caused to freely drink city water containing 1 mg/ml of NAC, were prepared. Further, the two groups of the-above-mentioned mice to which human recombinant IL-2 in an amount of 2 pg/0.5 ml/h was intraperitoneally administered twice a day, every two days for two weeks were provided. On day 14, the IL-12 production from MΦ was measured in the same manner as in Example 6.

Measurement of the GSH Content in MΦ Prepared:

The peritoneal cells were harvested from the mice which had undergone the respective treatments, and the GSH content in cells was analyzed by ACAS using an MCB reagent. In comparison with control mice (group caused to freely drink city water), the content of reductive glutathione was markedly increased in the group caused to freely drink NAC-containing city water and the IL-2 administration group, showing the image of reductive MΦ.

The content of reductive glutathione was more increased in the group which had undergone the combination of the free-drinking of NAC-containing city water and the IL-2 administration than in any of the group of the free drinking of NAC-containing city water and the IL-2 administration group. Thus, the effect brought forth by the combination of the treatments in the induction of reductive MΦ was clearly observed in the ACAS image analysis. In the group which had undergone the combination of the treatments, the increase in the content of reductive glutathione was observed in all MΦ's (in contrast with the fact that the increase in the content thereof in the group of the sole treatment was observed in from 40 to 50% of MΦ).

Function of MΦ Produced from each Group:

Peritoneal cells were harvested from four groups of the mice, and stimulated with LPS and IFNγ. Then, the NO production, the IL-6 production and the IL-12 production were measured. Since the content of reductive macrophage was increased in three groups of the sole administration and the combined administration in comparison with the control group, the amount of IL-6 in the macrophage culture supernatant was decreased (relative to 1,240 pg/ml in control mice, 320 pg/ml in the group caused to freely drink NAC-containing city water, 520 pg/ml in the IL-2 administration group, and 67 pg/ml in the group which had undergone the combination of the free-drinking of NAC containing city water and the IL-2 administration). In consideration of the fact that IL-6 is a main cytokine inducing Th2, the combination of the NAC oral intake and the injection of IL-2, the cytokine can control the Th1/Th2 balance more strongly. The increase pattern of the NO production was inversely related with the IL-6 production. With respect to the IL-12 production, the amount of IL-12 was 620 pg/ml in the group caused to freely drink NAC-containing city water, 946 pg/ml in the IL-2 administration group, and 2,386 pg/ml in the group which had undergone the free drinking of NAC-containing city water and the IL-2 administration in comparison with 0 pg/ml in control mice. Thus, the remarkable effect was observed by the combination of the treatments. It shows that the present invention provides the immunomodulator which is useful for the remarkable improvement of the immunological diseases such as rheumatoid arthritis in combination with the cytokines, and is therefore original and significant.

Example 9

Induction of Oxidative Macrophages through Administration of $(NAC-OMe)_2$, $(NAC)_2$ or Acetylgliotoxin Oxidative macrophages were induced by intraperitoneally administering 20 μg/0.5 ml/h of $(NAC-OMe)_2$ or $(NAC)_2$, or 10 μg/0.5 ml/h of acetylgliotoxin in DBA/2 mice on Day 1 and Day 2, and reductive macrophages were induced by intraperitoneally administering 2 mg/0.5 ml/h of NAC in DBA/2 mice on Day 1 and Day 2. This was clarified by harvesting peritoneal exudate cells 20 hours after the completion of the administration, adhering the cells to the plastic surface, then reacting the cells with 10 μM of monochlorobimane at 37° C. for 30 minutes, and analyzing the reaction product with ACAS. The increase in the amounts of oxidative macrophages can easily be determined visually from the fact that almost no reaction product with monochlorobimane is observed, namely, a gray or blue image is provided, and the increase in the amounts of reductive macrophages from the fact that a red or yellow image is provided respectively. It was found that macrophages induced 20 hours after subcutaneously administering 40 μg/0.1 ml/h of dexamethasone, a typical steroid having an immunosuppressive activity as well known on the back of a mouse on Day 1 and Day 2 gave almost a gray image, namely, oxidative macrophages were strongly induced. Meanwhile, the same examination was conducted by harvesting peritoneal exudate cells after 20 hours of the administration of 2 mg of N-acetylcystine (NAC). Consequently, a red or yellow image was obtained, and it was identified that reductive macrophages were induced. Similarly, the induction of oxidative macrophages was confirmed on ACAS, by intraperitoneally administering cystine derivatives, i.e., N,N'-diacetylcystine nitroxybutyl ester, N,N'-diacetylcystine dimethyl ester $(NAC-OMe)_2)$, N,N'-diacetylcystine diisopropyl ester $(NAC-OiPr)_2)$ and N,N'-di-L-alanylcystine dimethyl ester $(NAlaC-OMe)_2)$ (administering 20 μg/0.5 ml/h each, twice a week for three weeks, 9-11 weeks of age).

<Production of NO and IL-6 from Macrophages Induced through Administration of $(NAC-OMe)_2$, $(NAC)_2$ or Acetylgliotoxin>

Thus, the peritoneal exudate adherent cells were incubated in the following manner, and the amounts of NO and IL-12 produced in the culture supernatant were measured. With respect to the amount of IL-6, the amount of IL-6 produced spontaneously in the absence of a stimulator was measured.

(1) Materials

Cells: The peritoneal exudate adherent cells obtained by the stimulation, namely, the macrophages were added to a 96-well microplate in an amount of $1 \times 10^5$ cells/200 μl each.

Medium: Phenol red-free RPMI 1640: 200 μl/well

LPS: Lipopolysaccharide (made by Sigma Co.) (origin: *E. coli*) 100 ng/ml

IFNγ: 100 units/ml (2) Measuring method

Harvest of peritoneal MΦ:

Peritoneal cells were harvested by injecting 5 ml of a phenol red-free DMEM medium (supplied by Nikken Seibutsusha) ice-cooled into a peritoneal cavity of a mouse which had been put to sacrificial death with ether using an injection cylinder fitted with a 22-gauge needle, squeezing the same and pulling out the medium.

Determination of the amount of IL-6:

Conducted as in Example 2.

Measurement of a concentration of $NO_2$:

Conducted as in Example 2.

Determination of GSH in cells with ACAS:

Conducted as in Example 2.

Determination of an amount of IL-12:

Conducted as in Example 2.

Results:

The effects of inhibiting production of NO, IL-6 and IL-12 from macrophages are shown in Table 1.

TABLE 1

| | (Amount of produced relative to that of control group, %) | | |
|---|---|---|---|
| Sample | NO | IL-6 | IL-12 |
| $(NAC-OMe)_2$ | 12 | 320 | 11 |
| $(NAC)_2$ | 18 | 340 | 15 |
| Acetylgliotoxin | 22 | 450 | 14 |
| NAC | 172 | 42 | 920 |
| Dexamethasone | 45 | 1020 | 5 |

As is apparent from Table 1, the amounts of inflammatory cytokines IL-6, NO and IL-12 produced are changed with the oxidative macrophages induced through the administration of $(NAC-OMe)_2$, $(NAC)_2$ and acetylgliotoxin. That is, with the oxidative macrophages obtained through the administration of the agent, the IL-6 production is increased, and the production of NO, which induces tissue injury, and the production of IL-12, which increases the cellular immunity, are both decreased. This effect is the same as, or higher than, that of dexamethasone, a typical steroid-type immunosuppressant. On the contrary, with the reductive macrophages induced by N-acetylcysteine (NAC), the NO production and the IL-12 production are increased, and the IL-6 production is reduced.

Example 10

Effect of Inhibiting Delayed Type Hypersensitivity Reaction to Ovalbumin 20 g/0.5 ml/h of (NAC-OMe)$_2$, 20 g/0.5 ml/h of (NAC)$_2$, 2 mg/0.5 ml/h of NAC and 30 g/0.5 ml/h (Day 1) of dexamethasone were continuously administered from Day 1 to Day 5 as in Example 9. With respect to an antigen, 100 µl of a suspension of ovalbumin and Complete H37Ra Adjuvant (Difco) at a ratio of 1:1 (containing 250 µg of ovalbumin) were administered subcutaneously to the back as a sensitization antigen on Day 2 and to the left ear as an induction antigen on Day 8. After 24 hours, the thickness on the left ear was compared with that of the right ear.

The results of the effect of inhibiting the delayed type hypersensitivity reaction to the ovalbumin antigen are shown in Table 2. The administration of (NAC-OMe)$_2$ and (NAC)$_2$ remarkably inhibited the delayed type hypersensitivity reaction to the ovalbumin antigen. This reveals that the administration of these substances inhibits the cellular immunity.

TABLE 2

| Sample | Increase in the ear thickness (mm) |
|---|---|
| Control group | 15.1 |
| (NAC-OMe)$_2$ | 9.75 |
| (NAC)$_2$ | 9.88 |
| NAC | 16.5 |
| Dexamethasone | 4.75 |

Example 11

Function of Macrophages in an Animal in which a Gene is Knocked Out

For clarifying a mechanism of chronic or advanced inflammation, it is important to analyze, at a molecular level, why there is a difference in production of an inflammatory mediator or cytokine between oxidative MΦ and reductive MΦ. Generally, extracellular stimulation (ligand) is transferred into cells through a receptor present on cell surfaces. Various kinases are activated with a signal from a receptor, and transcriptional factors are also activated, translocated to the nucleus, and bound to target genes for expression. According to the recent studies, it is being clarified that a redox system in cells participates in activation of transcriptional factors, shifting of the same into the nucleus and binding of the same to genes (refer to Annual Rev. Immunology, vol.8, pp. 453-457, and Embo J., 10, pp. 2247-2251, 1991). At present, it is unknown how a redox system in cells participates in a gene expression system through a receptor in MΦ. As one approach for clarifying it, MΦ's were produced from knock out mice deficient in a molecule participating in a signal translocation system from a receptor, and the function of the redox system was analyzed. Specifically, a common γ chain (γc) used in common as a receptor constituting molecule of IL-2, IL-4, IL-7, IL-9 and IL-15 was used as a target molecule.

Cytokine and Stimulator:

As mouse IFNγ, a recombinant supplied by Genzyme was used. As human IL-2 and human IL-6, recombinants supplied by Ajinomoto Co. Inc. were used. As human IL-12, a recombinant supplied by Pharmingen was used.

As LPS, a substance derived from *E. coli* 055:B5 supplied by Difco was used. As lentinan, a preparation produced by Ajinomoto Co. Inc. was used.

Mice Used:

γc knock out mice were obtained from Professor Sugamura, Tohoku University Medical School.

As wild mice used for mating and as a control, C57BL/6 obtained from CRJ was used.

Measurement of the GSH Content in MΦ Produced from Knock Out Mice:

Peritoneal cells were harvested from γc knock out mice, and the GSH content in cells was analyzed by ACAS using an MCB reagent. The content of reductive glutathione in MΦ derived from γc knock out mice was remarkably decreased in comparison with that in control mice (C57BL/6).

Function of MΦ Harvested from Knock Out Mice:

Peritoneal cells were produced from wild mice (C57BL/6) and γc knock out mice, and stimulated with IPS, IL-2, IFNγ and a combination thereof. The NO production, the IL-6 production and the IL-12 production were measured. Almost no NO production was observed in any mice in the absence of stimulation. In the stimulation with the combination of LPS and IFNγ, the decreased NO production in γc knock out mice derived MΦ was observed to less than half that in control mice. Further, the IL-6 production was analyzed. In the LPS stimulation, an increase in the IL-6 production was observed in γc knock out mice (962 pg/ml relative to 81 pg/ml of a control). In the IFNγ stimulation, an increase in the IL-6 production was observed in γc knock out mice. Still further, the IL-12 production with the LPS stimulation and the IFNγ stimulation was examined. No production was observed at all in any mice. This proves that in the gene knock out mice used herein, the amount of the oxidative macrophages is increased to increase the humoral immunity or the allergic reaction mainly caused by Th2 and to decrease the cellular immunity supported by TH1. In the animal disease models, it is clearly shown that the invention is original and significant in the diagnosis of immunological diseases.

Example 12

Spontaneous Progression of Inflammatory Bowel Disease in γc Knock Out Mice

In wild-type normal littermates of γc knock out mice (genetic phenotypes +/+, +/Y), no inflammatory bowel disease is observed at all under ordinary SPF breeding conditions. However, in γc knock out mice (genetic phenotypes, –/–, –/+ and –/Y), inflammatory bowel diseases occur very often. With respect to homo-knock out mice with –/– and –/Y phenotypes, approximately 70% thereof are spontaneously accompanied with inflammatory bowel diseases within 4 months. Also with respect to mice with +/– phenotype, approximately 60% thereof are spontaneously accompanied therewith within 6 months. That is, intestinal shortening, bloody stool, diarrhea, loose passage, anal prolapse and colonal hypertrophy are observed.

With respect to an intestinal inflammation model, the oral intake of dextran sulfate is well known. However, an inflammatory image of γc knock out mice is by far similar to that observed in inflammatory bowel diseases of humans. In the histochemical analysis using pathologic samples, the following fact was clarified.

Analysis of pathologic specimens was conducted with respect to formalin-immobilized HE dyed specimens of the large intestine corresponding to the colon in a portion which was from 2 to 3 cm from the anus. The evaluation was conducted with respect to five points, 1) longitudinal spreading of inflammatory cell invasion in a direction of a mucous epithelium-lamina propria mucosae-lamina muscularis mucosae-submucous layer-internal circular layers of muscular tunics-external longitudinal layers of muscular tunics-serous membrane, 2) lateral spreading thereof, 3) types of invaded cells, 4) degree of neovascularization and 5) hypertrophy of a submucous layer. Invasion of inflammatory cells was scarcely observed in +/Y normal samples, wild-type littermates of γc knock out mice, and the mucous structure was retained almost intact in both goblet cells and mucous epithelium cells. In the group of the free drinking of 1% dextran sulfate water, drop of neutrophils and inflammatory cells in the gland cavity was observed, and degeneration and disappearance of goblet cells and metaplasia and degeneration of the mucous epithelium were identified at high levels. Invasion of lymphocytes, MΦ and neutrophils, neovascularization and vasodilation occurred at high levels. It was rated as grade 4.

In untreated samples of γc knock out mice with genotypes, the mucous epithelium was nearly intact, but hyperplasia was observed. Drop of inflammatory cells into the gland cavity did not occur. No edema was observed in the submucous layer, nor did invasion in the muscular tunics and the submucous layer occur. Invasion of MΦ and lymphocytes was observed only in the lamina propria mucosae, and unlike dextran sulfate-induced models, invasion of neutrophils was not observed. It was different from a mere acute inflammation image, and close to a human inflammatory bowel disease pathology image.

In untreated samples of γc knock out mice −/Y, the mucous epithelium was 2 or 3 times that of wild-type mice, and invasion of inflammatory cells was observed only in the lamina propria mucosae as a local cluster. The mucosa in contact with the cluster in the untreated samples of γc knock out mice +/− was close to the normal one compared with that of mice −/− and −/Y. The invasion cluster of inflammatory cells was observed in the bottom of the lamina propria mucosae only at a low level.

Accordingly, the intestinal inflammation of γc knock out mice with −/− and −/Y genotypes is similar to that of humans, and the dextran sulfate-induced model is considered different in mechanism from the γc knock out mouse spontaneous inflammatory bowel disease model.

Example 13

Effect of Inhibiting Spontaneous Inflammatory Bowel Diseases in γc Knock Out Mice On the basis of the findings mentioned above, the effect of inhibiting spontaneous progression of inflammatory bowel disease in γc knock out mice was examined with respect to human Crohn disease and ulcerative colitis models. Saline, (NAC-OMe)$_2$ or (NAC)$_2$ (20 μg/h) was administered twice a week, 5 times in total, to each of 6 γc knock out male mice with +/Y genotype and 6 γc knock out male mice with −/Y genotype which were inclined to have oxidative MΦ. It was examined whether or not the intestinal inflammation spontaneously progressed in −/Y was inhibited. In case of (NAC-OMe)$_2$, on Day 14 of the administration, the occurrence rate of the non-administration −/Y group and the administration −/Y group was 83% to 25%; on Day 31, the occurrence rate was 83% to 25%, and the survival rate was 33% to 100%; and on Day 45, the occurrence rate was 100% to 25%, and the survival rate was 33% to 75%. In case of (NAC)$_2$, it was 30, 40, 100, 40, 75% respectively. Thus, it was identified that the substance used in the invention clearly exhibited the effect to prolong survival of life and the effect of preventing the disease progression in the intestinal inflammation spontaneously induced. By the way, in the non-administration +/Y group and the administration +/Y group, the disease progression did not occur, and there was no difference therebetween.

Example 14

Effect of Inhibiting Dextran Sulfate-induced Inflammatory Bowel Disease in γc Knock Out Mice To 3-week-old γc knock out mice with +/− genotypes were administered 20 μg/h of (NAC-OMe)$_2$ three times a week for 2 weeks. On day 16, the free drinking of 1% dextran sulfate water was started. On Day 30, the occurrence rate of the inflammatory bowel disease was 100% in the non-administration group and 16.6% in the administration group, and the effect of the administration of this agent was observed. Further, the survival rate was 57% in the non-administration group and 100% in the administration group. Thus, the remarkable effect was observed. With respect to the +/+ mice, the occurrence rate was 60% in the administration group and 80% in the non-administration group. Therefore, the effect of the administration was also observed. The γc knock out mice and their wild-type male mice (+/Y- and −/Y) and female mice (+/+, +/− and −/−) were caused to freely drink water containing 1% dextran sulfate as a inflammatory bowel disease model. The female mice showed a resistance, and the order of the resistance was found to be −/Y and +/Y in male mice, and −/−, +/− and +/+ in female mice. After the start-up of the administration of dextran sulfate, the survival rate was 80, 0, 100, 100 and 40% on Day 13, showing that the mice mainly having oxidative MΦ were more resistant to the dextran sulfate-induced gastrointestinal inflammation. This indirectly proved the invention to be reasonable.

Example 15

Functions of Macrophages in Synovial Cells from Rheumatoid Arthritis Patients

So as to elucidate the mechanism of chronic exacerbation of inflammation, it is significant to analyze at a molecular level why the difference in the generation of an inflammatory mediators and cytokines emerges between oxidized MΦ and reduced MΦ. Generally, extracellular stimuli (ligands triggering) are intracellularly transmitted via specific receptors present on cell surface. Intracellular signals from the receptors activate various kinases and additionally activate transcriptional factors, so that the transcriptional factors translocate into nuclei and bind to the enhancer/promoter sequence of a target gene therein, leading to the expression thereof. Recent research works are under way of elucidating that intracellular redox systems are participating in activation, nuclear translocation and DNA binding of transcriptional factors [ANNUAL REV. IMMUNOLOGY, Vol. 8, 453-475 (1990); EMBO J., 10, 2247-2251 (1991)]. Up to now, however, it has not yet been elucidated how the intracellular redox systems are involved in the receptor-mediated gene expression systems of inflammatory mediators or cytokines in macrophages.

Cytokine and Stimulator:

As mouse IFNγ, a recombinant supplied by Genzyme was used. As human IL-2 and human IL-6, recombinants supplied by Ajinomoto Co. Inc. were used. As human IL-12, a recombinant supplied by Pharmingen was used.

As LPS, a substance derived from *E. coli* 055:B5 supplied by Difco was used. As lentinan, a preparation produced by Ajinomoto Co. Inc. was used.

Joint-derived Macrophages:

Synovial tissue was aseptically sampled from tissues resected during joint surgery. The sampled synovial tissue was rinsed in phosphate buffer, from which the surface was peeled off in a petri dish containing the same phosphate buffer. Then, the resulting synovial tissue was cut into pieces with a pair of scissors. To the pieces were added 2% hyaluronidase (manufactured by Sigma), 0.2% DNase (derived from bovine pancreas) and 5% collagenase, for enzymatic treatment at 37° C. for 2 hours. After discarding the resulting debris, a cell fraction recovered by centrifugation was adjusted to $5\times10^5$ cells/ml in a phenol red-free DMEM culture medium supplemented with 10% FCS (manufactured by Nikken Biology Co.). For 3 hours, the cells were allowed to adhere to the plastic surface. Plastic surface adherent macrophage-like cells harvested with a rubber policeman were then subjected to rinsing in combination with centrifugation three times using the culture medium under ice cooling. The resulting cells were designated as synovial tissue-derived macrophages and were then subjected to the following experiments.

Determination of the Amount of IL-6:

A stimulator was added to $1\times10^6$ MΦ, and the incubation was conducted at 37° C. for 2 days in a $CO_2$ incubator. After centrifugation, the culture supernatant was collected.

The amount of IL-6 was determined using IL-6 dependent mouse hybridoma MH60 cells (J. Eur. Immunol., vol. 18, p. 951, 1988). One hundred microliters of the culture supernatant were added to 100 μl of the MH60 cell suspension adjusted to $1\times10^5$ cells/ml in a 10% FCS-containing RPMI medium, and the mixed solution was incubated at 37° C. for 2 days in a $CO_2$ incubator. Subsequently, 10 μl of MTT (supplied by Sigma Co.) solution adjusted to a concentration of 5 mg/ml in the same medium were added thereto, and the reaction was conducted at 37° C. for 5 hours. After the completion of the reaction, the centrifugation was conducted. The supernatant (160 μl) was removed, and 100 μl of a mixture of hydrochloric acid and propanol were added to the residue. The suspension was conducted using a pipetman to dissolve the cells. Immediately after the dissolution, an absorbance of 570 nm was measured with an immunometer (supplied by Bio-Rad).

Measurement of a Concentration of $NO_2$:

A stimulator was added to $1\times10^5$ MΦ, and the incubation was conducted at 37° C. for 2 days in a $CO_2$ incubator. After the completion of the centrifugation, the culture supernatant was collected.

One hundred microliters of a Griess-Romijn reagent (supplied by Waco Pure Chemical Industries, Ltd.) adjusted to a concentration of 50 mg/ml in distilled water were added to 100 μl of the culture supernatant, and the reaction was conducted at room temperature for 15 minutes. After the completion of the reaction, an absorbance of 540 nm was measured. $NaNO_2$ was used as a standard.

Determination of GSH in Cells with ACAS:

Three-hundred microliters of a cell suspension adjusted to a concentration of $3\times10^5$ cells/ml in an RPMI 1640 medium (phenol red-free) were charged into a chambered coverglass (#136439, supplied by Nunc), and incubated at 37° C. for 2 hours using a $CO_2$ incubator. The culture solution was washed with the same medium, and 300 μl of monochlorobimane (supplied by Molecular Plobe) adjusted to 10 μM in the same medium were added thereto. The mixture was charged into a $CO_2$ incubator of 37° C., and the reaction was conducted for 30 minutes. The fluorescent intensity was measured with ACAS. In ACAS, a UV laser was used.

Determination of an Amount of IL-12:

The amount of IL-12 was determined through bioassay using cells of human T cell strain 2D6 (J. Leukocyte Biology, vol. 61, p. 346, 1997).

2D6 cells which had been incubated in an RPMI 1640 medium containing 500 pg/ml of recombinant human IL-12, 50 μM of 2-mercaptoethanol and 10% FCS (fetal calf serum) were moved to a tube, and centrifugally washed three times with the above-mentioned medium without IL-12 and cell density was adjusted to $1\times10^5$/ml. The cell suspension was added in an amount of 100 μl each to a 96-well flat bottom plate containing a sample serially diluted in advance with an RPMI 1640 medium containing 50 μM of 2-mercaptoethanol and 10% FCS in an amount of 100 μl each. Subsequently, the mixture was charged into a 5% $CO_2$ incubator of 37° C., and incubated for 48 hours. For final 6 hours, $^3$H-TdR was pulsed (a substance adjusted to 370 kBq/ml in an RPMI 1640 medium containing 50 μM of 2-mercaptoethanol and 10% FCS was added in an amount of 50 μl each). The cells were harvested, and the radioactivity was measured using a counter (Matrix 96, supplied by Packard).

Example 16

GSH Concentration in MΦ Prepared from Synovial Tissue from Rheumatoid Arthritis Patients By ACAS with an MCB reagent, the GSH concentration in the macrophage-like cells prepared by the aforementioned method was determined. The macrophages collected were suspended and adjusted in a phenol red-free RPMI 1640 culture medium supplemented with 10% fetal calf serum to $3\times10^6$ cells/ml; the suspension was divided in 100-μl portions on Lab-Tek Chamber Slide (#136439; manufactured by NUNC, CO.), for culturing in 5% $CO_2$ at 37° C. for 3 hours; after discarding the nonadherent cells, the serum-free culture medium of 200 μl was fed to the resulting culture, followed by addition of MCB (abbreviation for monochlorobimane) to a final concentration of 10 μM, for reaction for 30 minutes; and the amount of intracellular GSH was assayed by imaging analysis with an ACAS system (manufactured by Meridian Co.).

Results:

Reduced glutathione was quantitatively assayed by the ACAS method. In the macrophages derived from tissues of rheumatoid arthritis patients at active stage, compared with the macrophages derived from tissues of patients with osteoarthritis, the relative ratio of oxidative macrophages, namely macrophages with the reduced amount of glutathione, was increased. Because of the increase of oxidative macrophages, IL-6 in the culture supernatant of the macrophages was prominently increased. It is thus indicated that the identified redox state of macrophages on the basis of the glutathione content assay can suggest the pathological state and immune function of a rheumatoid arthritis patient in a simple and appropriate manner, with no need of determination of numerous functional parameters of macrophages. For the administration of the inventive anti-rheumatoid agent, thus, the pathological state and immune function of a patient can be examined and diagnosed according to the aforementioned macrophage classification method.

Function of MΦ Prepared from Joint Cavities of Rheumatoid Arthritis Patients:

Macrophages were prepared from synovial tissues of patients with osteoarthritis and rheumatoid arthritis patients at active stage by the same method as described above, which were then stimulated with LPS, IFNγ and a combination thereof for assaying the abilities of NO and IL-12 generation. With no stimulation, almost no IL-12 generation was observed in the macrophages from any of the origins; by stimulation with a combination of LPS and IFNγ, no such generation was observed therein. The level of NO generation in the macrophages from patients with active-stage rheumatoid arthritis was decreased ½-¼-fold the level in the control, which indicates that oxidative macrophages predominant in the rheumatoid arthritis patients at active stage potentiate humoral immune response driven by Th2, while cellular immune response for which Th1 is responsible is declined in these patients. The findings described above suggest that the pathological state of rheumatoid arthritis patients can be diagnosed by assaying the GSH content in macrophages, which is beneficial to determine the way for the administration and application of the inventive anti-rheumatoid agent. Thus, the creativeness and significance of the invention can thus be exemplified.

Example 17

Modification of Macrophage Redox Function with Addition of Chemical Agents to Culture System of Macrophage-like Cells from Tissues of Rheumatoid Arthritis Patients By the same manner as in Example 3, macrophage-like cells were collected from tissues of rheumatoid arthritis patients, and were then suspended and adjusted in a phenol red-free RPMI 1640 culture medium supplemented with 10% fetal calf serum to 3×10$^6$ cells/ml. The suspension was divided in 100-μl portions on Lab-Tek Chamber Slide (#136439; manufactured by NUNC, CO.), for culturing in 5% $CO_2$ at 37° C. for 3 hours; after discarding the nonadherent cells, the 200-μl serum-free culture medium further containing any of the following chemical agents was fed to the resulting culture, for reaction for 3 hours; and then, the resulting culture was rinsed three times, followed by addition of the serum-free culture medium of 200 μl and addition of monochlorobimane to a final concentration of 10 μM, for reaction for 30 minutes. The amount of intracellular GSH was assayed by imaging analysis with an ACAS system (manufactured by Meridian Co.).

Results:

Reduced glutathione was quantitatively assayed by the ACAS method. In the glutathione ethyl ester (2 mM)-added group compared with the control physiological saline-added group, the relative ratio of oxidative macrophages, namely macrophages with the reduced amount of intracellular glutathione, was decreased. Because of the increase of reductive macrophages, IL-6 in the culture supernatant of the macrophages was prominently decreased. The same action was also observed in groups with addition of γ-glutamylcysteine dimethyl ester, N-acetylcysteine nitroxybutyl ester, glutathione monoethyl ester, glutathione nitroxybutyl ester and glutathione diethyl ester (all added at 2 mM). The induction of oxidative macrophage with the reduced amount of intracellular glutathione was confirmed in groups with addition of cystine derivatives such as N,N'-diacetylcystine nitroxybutyl ester, N,N'-diacetylcystine dimethyl ester [(NAC-OMe)$_2$], N,N'-diacetylcystine diisopropyl ester [(NAC-OiPr)$_2$], and N,N'-di-L-alanylcystine dimethyl ester [(NAlaC-OMe)$_2$] (all added at 2 μM).

Example 18

Effects of Chemical Agents Administered to Rats with Adjuvant-induced Arthritis (AA)

Adjuvant-induced arthritis was triggered in Lewis rats in a conventional manner; and the effects of chemical agents were examined in the animals. Adjuvant-induced arthritis is well known as an experimental arthritis inducible in rats [Taurog et al., Meth. Enzymol. 162, 339-355 (1988)]. It is suggested that clinical efficacy of non-steroidal acid anti-inflammatory agents and immunosuppressive agents such as cyclosporin, cyclophosphamide and methotrexate as anti-rheumatoid agents can be reflected in the model. An adjuvant is administered at 1 mg/0.1 ml per rate at a site of caudal root. The edema reaches its peak about 2 to 3 weeks after the administration of the adjuvant. The edema is triggered by inflammatory infiltration of monocytes. Swollen joints are measured with a micrometer every day; comparing the diameters of the joints prior to and after adjuvant administration and after initiation of the treatment with chemical agents with the diameters of the joints in the control group, the effects of the chemical agents were expressed as the ratio in % of joint swelling in the experimental groups to joint swelling in the control group. The effects were determined on day 15 after adjuvant administration. The chemical agents were given, starting the day next to the day of adjuvant administration, and every 3 days thereafter. The results are shown in Table 3.

TABLE 3

| Chemical Agents | Ratio in % of joint swelling in experimental groups to joint swelling in control group |
| --- | --- |
| Physiological saline | 100 |
| (NAC-OMe)$_2$ | 50 |
| (NAC)$_2$ | 96 |
| NAC | 132 |
| Lentinan | 52 |

The results based on the experiments of drug efficacy apparently indicate that adjuvant-induced arthritis can be suppressed by the administration of a substance inducing oxidative macrophages. A single dose is 1 mg/kg for (NAC)$_2$ and (NAC-OMe)$_2$; 100 mg/kg for NAC; and 0.1 mg/kg for lentinan.

Example 19

Effects of Administration of Chemical Agents, Including Oral Administration Thereof Adjuvant-induced arthritis was induced in Lewis rats in a conventional manner. In the same manner as in Example 11, the effects of chemical agents were examined in these rats. The conditions were the same as described above. The results are shown in Table 4.

TABLE 4

| Chemical Agents | Ratio in % of joint swelling in experimental groups to joint swelling in control group |
|---|---|
| Physiological saline | 100 |
| Intravenous (NAC-OMe)$_2$ | 42 |
| Intravenous (NAlaC-OMe)$_2$ | 45 |
| Intravenous (NAC)$_2$ | 95 |
| Oral NAC | 142 |
| Intraperitoneal γ-glutamylcysteine dimethyl ester | 120 |
| Intraperitoneal glutathione diethyl ester | 132 |
| Intravenous lentinan | 50 |

The doses were similar to those in Example 11; the doses of (AlaC-OMe)$_2$, γ-glutamylcysteine dimethyl ester, and glutathione diethyl ester were all 100 mg/kg.

The above results apparently indicate that compounds represented by the structural formula 1, including N,N'-diacetylcystine [(NAC)$_2$], N,N'-dipropylcystine [(NPC)$_2$], N,N'-diacetylcystine dimethyl ester [(NAC-OMe)$_2$], N,N'-diacetylcystine diisopropyl ester [(NAC-OiPr)$_2$] and N,N'-di-L-alanylcystine dimethyl ester [(NAlaC-OMe)$_2$], and nitroxybutyl esters thereof and exerting actions to decrease the content of reduced glutathione in macrophages, suppress delayed type hypersensitivity reactions, and suppress the generation of IFNγ or IL-12, are pharmacologically effective when administered to animals with adjuvant-induced arthritis.

Even when the compounds were administered 3 times per week for 3 weeks, the effects on the suppression of joint swelling were also observed in model mice with the spontaneous onset of rheumatoid arthritis. In the model mice, swelling of foreleg finger bone joints was started on age 2 months, together with pannus formation in the synovial tissue of the joints under observation; by the dosing of the compounds with actions to decrease the content of reduced glutathione in macrophages, suppress delayed type hypersensitivity reactions, and suppress the generation of IFNγ or IL-12 to the animals, however, the joint score 4.5 months later was suppressed to 40 to 50% of the score in the physiological saline-dosed control group. Alternatively, it is revealed that joint swelling is enhanced by reductive macrophage-inducing substances including glutathione precursors such as γ-glutamylcysteine, γ-glutamylcysteine dimethyl ester, and N-acetylcysteine nitroxybutyl ester, and glutathione derivatives such as glutathione monoester, glutathione nitroxybutyl ester and glutathione diester.

Example 20

Functions of Macrophages in NOD Mice with Spontaneous Diabetes Mellitus

So as to elucidate the mechanism of chronic exacerbation of inflammation, it is significant to analyze at a molecular level why the difference in the generation of an inflammatory mediators and cytokines emerges between oxidized MΦ and reduced MΦ. Generally, extracellular stimuli (ligands triggering) are intracellularly transmitted via specific receptors present on cell surface. Intracellular signals from the receptors activate various kinases and additionally activate transcriptional factors, so that the transcriptional factors translocate into nuclei and bind to the enhancer/promoter sequence of a target gene therein, leading to the expression thereof. Recent research works are under way of elucidating that intracellular redox systems are participating in activation, nuclear translocation and DNA binding of transcriptional factors [ANNUAL REV. IMMUNOLOGY, Vol. 8, 453-475 (1990); EMBO J., 10, 2247-2251 (1991)]. Up to now, however, it has not yet been elucidated how the intracellular redox systems are involved in the receptor-mediated gene expression systems of inflammatory mediators or cytokines in macrophages.

Cytokine and Stimulator:

As mouse IFNγ, a recombinant supplied by Genzyme was used.

As human IL-2 and human IL-6, recombinants supplied by Ajinomoto Co. Inc. were used. As human IL-12, a recombinant supplied by Pharmingen was used.

As LPS, a substance derived from *E. coli* 055:B5 supplied by Difco was used. As lentinan, a preparation produced by Ajinomoto Co. Inc. was used.

Mice Used:

NOD mice as model animals of insulin-dependent diabetes mellitus were purchased from Nippon Clair, Co. Among them, female mice were mainly used. Wild-type ICR mice purchased from Nippon Charles River, Co. (CRJ) were used as controls. Insulin-non-dependent diabetes mellitus-diseased animals were db/db mice purchased from Nippon Clair, Co.

Harvest of Peritoneal MΦ:

Peritoneal cells were harvested by injecting 5 ml of a phenol red-free DMEM medium (supplied by Nikken Seibutsusha) ice-cooled into a peritoneal cavity of a mouse which had been put to sacrificial death with ether using an injection cylinder fitted with a 22-gauge needle, squeezing the same and pulling out the medium.

Determination of the amount of IL-6:
Measurement of a concentration of NO$_2$:
Determination of GSH in cells with ACAS:
Determination of an amount of IL-12:

These were conducted in the same manner as in Example 15.

Measurement of the GSH Content in MΦ Produced from NOD Mice:

Peritoneal cells were prepared according to the method stated above, and the GSH content in cells was analyzed by ACAS using an MCB reagent. The content of reductive glutathione was clearly decreased in the NOD mice at the age of 3-5 weeks, and was clearly increased in those accompanied with the disease (diabetes), as compared with control mice.

Function of MΦ Produced from NOD Mice:

Peritoneal cells were prepared from wild mice and NOD mice, and stimulated with LPS, IL-2, IFNγ and a combination thereof. The NO production and the IL-12 production were measured. Almost no IL-12 production was observed in any mice derived MΦ in the absence of stimulation. In the stimulation with the combination of LPS and IFNγ, no IL-12 production was observed in the NOD mice at the age of 3-5 weeks, but the IL-12 production was observed in those accompanied with the disease. The NO production was decreased to from one third to one fourth in the NOD mice at the age of 3-5 weeks, but was increased to from two to three times in those accompanied with the disease, as compared with control mice. This proves that in the NOD mice used herein as a model of spontaneous diabetic mellitus, the oxidative macrophages are predominant at the stage of infiltration of inflammatory cells in pancreatic islet, thereby increasing the humoral immune response mainly caused by Th2 and decreasing the cellular immune response supported by Th1. On the other hand, reductive macrophages are predominant at the stage of occurrence of diabetes and deficient insulin secretion by destruction of islets of Langerhans, thereby increasing the cellular immune response mainly caused by Th1 and decreasing the humoral immune response supported by Th2. In the animal disease models, it is clearly shown that the anti-diabetes agent provided by the present invention and the diagnosis of diseases required for applying the agent is original and significant.

Example 21

Redox States of Macrophage in NOD Mice

Method:

Macrophages were sampled from the abdominal cavities of the NOD mice and the control mice, to identify whether the macrophages were of an oxidative form or a reductive form. After physiological saline of 5 ml was administered intraperitoneally into these mice, intraperitoneal macrophages were collected, which were then suspended and adjusted in a phenol red-free RPMI 1640 culture medium supplemented with 10% fetal calf serum to $3 \times 10^6$ cells/ml. The suspension was divided in 100-μl portions on Lab-Tek Chamber Slide (#136439; manufactured by NUNC, Co.), for culturing in 5% $CO_2$ at 37° C. for 3 hours; after discarding the nonadherent cells, the serum-free culture medium of 200 μl was fed to the resulting culture, followed by addition of MCB (abbreviation for monochlorobimane) to a final concentration of 10 μM for reaction for 30 minutes; and based on UV absorption, GSH was assayed by imaging analysis with an ACAS system (manufactured by Meridien Co.).

Results:

Reduced type of glutathione was quantitatively assayed by the ACAS method. In the NOD mice of age 3 to 5 weeks compared with the control mice, the relative ratio of oxidative macrophages, namely macrophages with the reduced amount of intracellular glutathione, was increased. Because of the increase of oxidative macrophages, IL-6 in the culture supernatant of the macrophages was prominently increased (at 430 pg/ml vs at 120 pg/ml in the control mice). In the mice with the onset of the diabetes, macrophages with increased amount of intracellular reduced glutathione, namely reductive macrophages, were relatively increased. It is thus indicated that the identified redox state of macrophages on the basis of the glutathione content assay can suggest the pathological conditions and immune function of a diabetic patient in a simple and appropriate manner, with no need of determination of numerous functional parameters of macrophages. For the administration of the inventive anti-diabetes mellitus agent, thus, the pathological conditions and immunological state of a diabetic patient can be examined and diagnosed according to the aforementioned macrophage classification method.

Example 22

Induction of Reductive Macrophages by Chemical Agents Administered to NOD Mice of Age 3 to 5 Weeks Through a probe, glutathione ethyl ester was orally given at 1 mg/0.5 ml/h/day to the NOD mice of age 4 weeks on alternate days, in total five times. By the same method as in Example 3, intraperitoneal cells were collected from the mice to sample intraperitoneal macrophages, which were then suspended and adjusted in a phenol red-free RPMI 1640 culture medium supplemented with 10% fetal calf serum to $3 \times 10^6$ cells/ml. The suspension was divided in 100-μl portions on Lab-Tek Chamber Slide (#136439; manufactured by NUNC, Co.), for culturing in 5% $CO_2$ at 37° C. for 3 hours; after discarding the nonadherent cells, the serum-free culture medium of 200 μl was added to the resulting culture, followed by addition of MCB (abbreviation for Monochlorobimane) to a final concentration of 10 μM for reaction for 30 minutes; and based on UV absorption, intracellular GSH was assayed by imaging analysis with an ACAS system (manufactured by Meridian Co.).

Results:

Reduced glutathione was quantitatively assayed by the ACAS method. In the NOD mice dosed with glutathione ethyl ester, compared with the control NOD mice administered with physiological saline, the relative ratio of oxidative macrophages, namely macrophages with the decrease in the content of reduced glutathione, was decreased. Because of the increase of reductive macrophages, IL-6 in the culture supernatant of the macrophages was prominently decreased (at 460 pg/ml in the NOD mice vs at 3800 pg/ml in the control group). It is thus indicated that the redox state of macrophages can be improved by glutathione ethyl ester orally administered. The same action is also observed for intraperitoneal dosing of γ-glutamylcysteine dimethyl ester (2 mg/0.5 ml/animal, administered on alternate days, in total five times, starting from the age 4 weeks), intraperitoneal dosing of N-acetylcysteine nitroxybutyl ester (0.5 mg/0.5 ml/animal, administered on alternate days in total five times, starting from the age 4 weeks), oral dosing thereof (1 mg/0.5 ml/animal, administered on alternate days, in total five times, starting from the age 4 weeks), intraperitoneal or oral dosing of glutathione monoethyl ester (2 mg/0.5 ml/animal, administered on alternate days, in total five times, starting from the age 4 weeks), intraperitoneal or oral dosing of glutathione nitroxybutyl ester (0.5 mg/0.5 ml/animal, administered on alternate days, in total five times, starting from the age 4 weeks), intraperitoneal or oral dosing of glutathione diethyl ester (2 mg/0.5 ml/animal, administered on alternate days, in total six times, starting from the age 3 weeks), and intraperitoneal dosing of lipoic acid (4 mg/0.5 ml/animal, administered on alternate days, in total five times, starting from the age 4 weeks).

Example 23

Effects of Chemical Agents Administered to NOD Mice Aged 3 to 6 Weeks at a Stage of Macrophages at Oxidized State and with Potential Occurrence of Inflammatory Cell Infiltration in Pancreatic Islet NOD mice purchased from Nippon Clair, Co. were naturally mated together. Among the off spring mice, a colony of NOD mice with a high frequency of the spontaneous onset of insulin-dependent diabetes mellitus was established. Female NOD mice from the colony were used for the present experiment. Chemical agents were orally or intraperitoneally administered to the NOD mice aged 3 to 6 weeks three times per week, in total nine times; and based on the test results of urine glucose, positive or negative, the onset of diabetes mellitus was followed once per week. Urine glucose was detected, using Uropaper (BM Test Glucose 5000, manufactured by Yamanouchi Pharmaceuticals, Co. Ltd.).

The results are shown in Table 5.

TABLE 5

| Chemical Agents | Frequency (%) of onset of diabetes mellitus *a | Frequency (%) of onset of diabetes mellitus *b |
|---|---|---|
| Physiological saline | 50 | 80 |
| (NAC-OMe)$_2$ | 70 | 80 |
| (NAC)$_2$ | 60 | 80 |
| Oral NAC | 30 | 40 |
| Intraperitoneal NAC | 10 | 20 |
| Lentinan | 10 | 20 |
| GSHOEt | 0 | 5 |

*a. on age 18 weeks
*b. on age 22 weeks

Chemical agents were administered intraperitoneally, unless otherwise stated.

The aforementioned results based on the experiments of drug efficacy apparently indicate that reductive macrophage-inducing substances including glutathione precursors such as γ-glutamylcysteine, γ-glutamylcysteine dimethyl ester, and N-acetylcysteine nitroxybutyl ester, glutathione derivatives such as glutathione monoethyl ester, glutathione nitroxybutyl ester and glutathione diethyl diester, and β(1-3)-linked glucans such as lentinan can suppress the spontaneous onset of diabetes mellitus in NOD mice of age 3 to 6 weeks at a stage of macrophages at oxidized state and with potential occurrence of inflammatory cell infiltration in pancreatic islet. (NAC)$_2$ and (NAC-OMe)$_2$ were at a single dose of 20 µg/animal; and NAC and GSHOEt were at a single dose of 2 µg/animal; and a single dose of lentinan was 0.1 mg/kg.

Example 24

Effects of Chemical Agents Administered to NOD Mice of Age 3 to 6 Weeks at a Stage of Macrophages at Oxidized State and with Potential Occurrence of Inflammatory Cell Infiltration in Pancreatic Islet and to Age 9 to 11 Weeks NOD mice purchased from Nippon Clair, Co. were naturally mated together. Among the off spring mice, a colony of NOD mice with a high frequency of the spontaneous onset of insulin-dependent diabetes mellitus was established. Female NOD mice from the colony were used for the present experiment. Chemical agents were orally or intraperitoneally administered to the NOD mice of age 3 to 6 weeks three times per week and to the NOD mice of age 9 to 11 weeks twice per week, in total 15 times; and based on the test results of urine glucose, positive or negative, the onset of diabetes mellitus was followed once per week. Urine glucose was detected, using Uropaper (BM Test Glucose 5000, manufactured by Yamanouchi Pharmaceuticals, Co. Ltd.).

The results are shown in Table 6.

| Chemical agents | Frequency (%) of onset of diabetes mellitus |
|---|---|
| Physiological saline | 60 |
| Intraperitoneal (NAC-OMe)$_2$ (20 µg/h) | 70 |
| Oral NAC (2 mg/h) | 40 |
| Intraperitoneal γ-glutamylcystein dimethyl ester (1 mg/h) | 10 |
| Oral γ-glutamylcysteine dimethyl ester (1 mg/h) | 20 |
| Intraperitoneal glutathione monoethyl ester (1 mg/h) | 0 |
| Intraperitoneal glutathione diethyl ester (1 mg/h) | 0 |
| Lentinan (0.1 mg/kg) | 0 |
| Oral glutathione diethyl diester (5 mg/h) | 0 |

The onset was judged on week 22.

The aforementioned results based on the experiments of drug efficacy apparently indicate that reductive macrophage-inducing substances including glutathione precursors such as γ-glutamylcysteine, γ-glutamylcysteine dimethyl ester, and N-acetylcysteine nitroxybutyl ester, glutathione derivatives such as glutathione monoethyl ester, glutathione nitroxybutyl ester and glutathione diester and β(1-3)-linked glucans such as lentinan, can suppress the spontaneous onset of inflammation of pancreatic islet and that of diabetes mellitus owing to the suppression of inflammatory cell infiltration into pancreatic islet, when these substances are administered to NOD mice of age 3 to 6 weeks at a stage of macrophages at oxidized state and with potential occurrence of inflammatory cell infiltration in pancreatic islet, and to age 9 to 11 weeks at a stage of induction of reductive macrophages.

Example 25

Effects of Chemical Agents Administered to NOD Mice Aged 9 to 11 Weeks at a Stage of Macrophages at Reduced State NOD mice purchased from Nippon Clair, Co. were naturally mated together. Among the off spring mice, a colony of NOD mice with a high frequency of the spontaneous onset of insulin-dependent diabetes mellitus was established. Female NOD mice from the colony were used for the present experiment. Chemical agents were orally or intraperitoneally administered to the NOD mice aged 9 to 11 weeks three times per week, in total nine times; and based on the test results of urine glucose, positive or negative, the onset of diabetes mellitus was followed once per week. Urine glucose was detected, using Uropaper (BM Test Glucose 5000, manufactured by Yamanouchi Pharmaceuticals, Co. Ltd.).

The results are shown in Table 7.

TABLE 7

| Chemical Agents | Frequency (%) of onset of diabetes mellitus |
|---|---|
| Physiological Saline | 67 |
| Intraperitoneal (NAC-OMe)$_2$ | 11 |
| (NAlaC-OMe)$_2$ | 11 |
| (NAC)$_2$ | 60 |
| Oral NAC | 60 |
| Intraperitoneal γ-Glutamylcysteine dimethyl Ester | 55 |

TABLE 7-continued

| Chemical Agents | Frequency (%) of onset of diabetes mellitus |
|---|---|
| Intraperitoneal glutathione diethyl ester | 67 |
| Lentinan | 50 |

The onset was judged on week 22; the doses were the same as in Example 24.

The aforementioned results apparently indicate that compounds represented by the structural formula 1, including N,N'-diacetylcystine [(NAC)$_2$], N,N'-dipropylcystine [(NPC)$_2$], N,N'-diacetylcystine dimethyl ester [(NAC-OMe)$_2$], N,N'-diacetylcystine diisopropyl ester [(NAC-OiPr)$_2$] and N,N'-di-L-alanylcystine dimethyl ester [(NAlaC-OMe)$_2$], and nitroxybutyl esters thereof and exerting actions to decrease the content of reduced glutathione in macrophages, suppress delayed type hypersensitivity reactions, and suppress the production of IFNγ or IL-12, can exert drug efficacy when these compounds are administered to the NOD mice aged 9 to 11 weeks at a stage of macrophages at reduced state.

Example 26

Effects of Chemical Agents in db/db Mice db/db mice purchased from Nippon Clair, Co. were naturally mated together. Among the offspring mice, a colony of db/db mice with a high frequency of the spontaneous onset of insulin-non-dependent diabetes mellitus was established. Male db/db mice from the colony were used for the present experiment. Chemical agents were intraperitoneally administered to the db/db mice aged 4 to 9 weeks three times per week, in total 18 times; and based on the level of blood sugar in the mice at satiation, the effects of the chemical agents on the improvement of the diseased conditions of insulin-non-dependent diabetes mellitus were followed once per week.

The results are shown in Table 8.

TABLE 8

| Chemical Agents | Relative ratio % of blood sugar level | | |
|---|---|---|---|
| | 6 weeks | 7 weeks | 8 weeks |
| Physiological saline | 100 | 100 | 100 |
| (NAC-OMe)$_2$ | 94 | 92 | 93 |
| (NAC)$_2$ | 95 | 100 | 98 |
| γ-Glutamylcysteine dimethyl ester | 85 | 65 | 60 |
| Glutathione diethyl ester | 82 | 62 | 60 |
| Lentinan + glutathione diethyl ester | 70 | 55 | 50 |

The doses were the same as in Example 24.

The aforementioned results based on the experiments of drug efficacy apparently indicate that when administered to the db/db mice at a high frequency of the spontaneous onset of insulin-non-dependent diabetes mellitus, these reductive macrophage-inducing substances including glutathione precursors such as γ-glutamylcysteine, γ-glutamylcysteine dimethyl ester, and N-acetylcysteine nitroxybutyl ester, glutathione derivatives such as glutathione monoester, glutathione nitroxybutyl ester and glutathione diester, and β(1-3)-linked glucans such as lentinan, significantly decrease the blood sugar level and effectively ameliorate the diseased conditions of insulin-non-dependent diabetes mellitus with the etiology of poor glucose incorporation into muscle and fat cells. The action mechanism is not yet elucidated, but the pharmacological effects may possibly be ascribed to the improvement of liver function or the inhibitory action against phosphatase.

Obviously, numerous modifications and variations of the present invention are possible in light of the above teachings. It is therefore to be understood that within the scope of the appended claims, the invention may be practiced otherwise than as specifically described herein.

U.S. patent application Ser. No. 09/181,881, filed on Oct. 29, 1998, is incorporated herein by reference.

Japanese Patent Application Serial No. 308300, filed on Oct. 29, 1998, is incorporated herein by reference.

Japanese Patent Application Serial No. 9-312727, filed on Oct. 27, 1997, is incorporated herein by reference.

What is claimed is:

1. A method of treating gastrointestinal inflammatory disease, hepatitis, or hepatic cirrhosis, comprising administering to a subject in need thereof an effective amount of
   (1) a cystine derivative represented by formula (I):

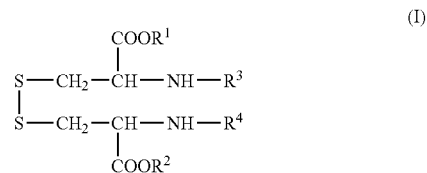

wherein
   R$^1$ and R$^2$, independently from each other, represent an alkyl group or an alkyl group substituted with a nitroxylbutyl group, and
   R$^3$ and R$^4$, independently from each other, represent an acyl group or a peptidyl group; and
   (2) at least one of Il-4 or TGF-beta,
   wherein administration of (1) and (2) (a) reduces the content of reductive glutathione in macrophages in the subject, (b) increases the capability of the macrophages to produce IL-6, and (c) decreases the capability of the macrophages to produce IL-12 and NO.

2. The method of claim 1, wherein IL-4 is administered to the subject.

3. The method of claim 1, wherein TGF-beta is administered to the subject.

4. The method of claim 1, wherein the subject is suffering from gastrointestinal inflammatory disease.

5. The method of claim 1, wherein the subject is suffering from hepatitis.

6. The method of claim 1, wherein the subject is suffering from hepatic cirrhosis.

7. The method of claim 1, wherein the subject is also suffering from rheumatoid arthritis.

8. The method of claim 1, wherein the intracellular content of reductive glutathione is reduced to at most 0.1 nmoles of glutathione per 5×10$^5$ macrophage cells.

9. The method of claim 1, wherein the alkyl group has 1 to 12 carbon atoms.

10. The method of claim 1, wherein the acyl group has into 12 carbon atoms.

11. The method of claim 1, wherein the peptidyl group has 1 to 10 amino acids.

12. A method of treating a cachectic condition caused by one or more conditions selected from the group consisting of cancers, diabetes, gastrointestinal inflammatory diseases, chronic rheumatoid arthritis, hepatitis, hepatic cirrhosis, hypersensitive interstitial pneumonia, pulmonary fibrosis, and autoimmune inflammatory diseases, comprising administering to a subject in need thereof an effective amount of a cystine derivative represented by formula (I):

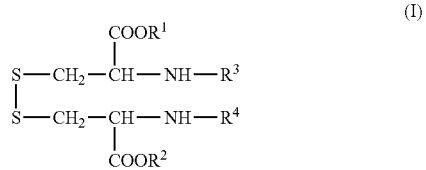

wherein
- $R^1$ and $R^2$, independently from each other, represent an alkyl group or an alkyl group substituted with a nitroxylbutyl group, and
- $R^3$ and $R^4$, independently from each other, represent an acyl group or a peptidyl group, wherein at least one of $R^3$ and $R^4$ is a peptidyl group having into 10 amino acids, wherein administration of the cystine deriviative (a) reduces the content of reductive glutathione in macrophages in the subject, (b) increases the capability of the macrophages to produce IL-6, and (b) decreases the capability of the macrophages to produce IL-12 and NO.

13. The method of claim 12, wherein $R^3$ is a peptidyl group having into 10 amino acids.

14. The method of claim 12, wherein $R^4$ is apeptidyl group having into 10 amino acids.

15. The method of claim 12, wherein the intracellular content of reductive glutathione is reduced to at most 0.1 nmoles of glutathione per $5 \times 10^5$ macrophage cells.

16. The method of claim 12, wherein the subject is suffering from chronic rheumatoid arthritis.

17. The method of claim 12, further comprising administering IL-4 to the subject.

18. The method of claim 12, further comprising administering TGF-beta to the subject.

19. The method of claim 12, wherein the alkyl group has 1 to 12 carbon atoms.

20. The method of claim 12, wherein the acyl group has into 12 carbon atoms.

21. The method of claim 12, wherein the peptidyl group has 1 to 10 amino acids.

22. The method of claim 12, wherein the acyl group is derived from a hydrocarbon carboxylic acid.

* * * * *

UNITED STATES PATENT AND TRADEMARK OFFICE
CERTIFICATE OF CORRECTION

PATENT NO. : 7,378,387 B2
APPLICATION NO. : 11/097146
DATED : May 27, 2008
INVENTOR(S) : Hamuro et al.

It is certified that error appears in the above-identified patent and that said Letters Patent is hereby corrected as shown below:

On the title page, Item (63), the Related U.S. Application Data is incorrect. Item (63) should read:

Related U.S. Application Data

-- (63) Continuation of application No. 09/731,830 filed on Dec. 8, 2000, now abandoned, which is a continuation of application No. 09/334,647, filed on Jun. 17, 1999, now Pat. No. 6,197,749, which is a continuation-in-part of application No. 09/181,881, filed on Oct. 29, 1998, now abandoned. --

Signed and Sealed this

Sixth Day of October, 2009

David J. Kappos
*Director of the United States Patent and Trademark Office*